United States Patent
Byun et al.

(10) Patent No.: US 10,392,178 B2
(45) Date of Patent: Aug. 27, 2019

(54) PREPARING BEVERAGES CONTAINING CANNABINOIDS USING BEVERAGE CONTAINERS WITH POLYMER MATRICES

(71) Applicant: ZEN POTION, INC., Pleasanton, CA (US)

(72) Inventors: Seung Young Byun, Pleasanton, CA (US); Willem Sloof, Veldhoven (NL)

(73) Assignee: ZEN POTION, INC., Pleasanton, CA (US)

( * ) Notice: Subject to any disclaimer, the term of this patent is extended or adjusted under 35 U.S.C. 154(b) by 177 days.

(21) Appl. No.: 15/305,628

(22) PCT Filed: Apr. 20, 2015

(86) PCT No.: PCT/US2015/026710
§ 371 (c)(1),
(2) Date: Oct. 20, 2016

(87) PCT Pub. No.: WO2015/164279
PCT Pub. Date: Oct. 29, 2015

(65) Prior Publication Data
US 2017/0043932 A1    Feb. 16, 2017

Related U.S. Application Data

(60) Provisional application No. 61/982,278, filed on Apr. 21, 2014, provisional application No. 61/992,745,
(Continued)

(51) Int. Cl.
*B65D 81/32*    (2006.01)
*B65D 41/50*    (2006.01)
(Continued)

(52) U.S. Cl.
CPC .............. *B65D 81/32* (2013.01); *A23L 2/52* (2013.01); *A61K 9/0095* (2013.01); *A61K 31/05* (2013.01);
(Continued)

(58) Field of Classification Search
CPC .......... B65D 2081/001; B65D 81/32–81/3283; B65D 41/32–41/58; B65D 25/08;
(Continued)

(56) References Cited

U.S. PATENT DOCUMENTS

| 129,652 A | 7/1872 | Codd |
| 3,779,372 A | 12/1973 | De Lloret |

(Continued)

FOREIGN PATENT DOCUMENTS

| JP | H0853135 A | 2/1996 |
| WO | WO 2013/009928 A1 | 1/2013 |
| WO | WO 2013/119679 A2 | 8/2013 |

OTHER PUBLICATIONS

Zen Potion, Inc., International Search Report and Written Opinion, PCT/US2015/026710, dated Jul. 28, 2015, 9 pgs.
Zen Potion, Inc., International Preliminary Report on Patentability, PCT/US2015/026710, dated Oct. 25, 2016, 8 pgs.

*Primary Examiner* — Drew E Becker
(74) *Attorney, Agent, or Firm* — Morgan, Lewis & Bockius LLP

(57) ABSTRACT

A beverage container includes a hollow container with a first reservoir and a second reservoir positioned within the hollow container, the first reservoir configured to store an aqueous beverage, the second reservoir sealingly storing one or more polymer matrices that include cannabinoid compounds, the second reservoir being configured to release the one or more polymer matrices into the aqueous beverage subsequent to the second reservoir being opened, the hollow container defining an opening through which a liquid in the
(Continued)

hollow container is allowed to egress from the hollow container. The beverage container also includes a closure sealingly and operably coupled with the opening of the hollow container, the closure operably coupled with the second reservoir such that opening of the closure initiates opening of the second reservoir, the closure sealing the opening of the hollow container. Methods of using the beverage container and preparing a beverage containing cannabinoids are also described.

10 Claims, 18 Drawing Sheets

Related U.S. Application Data filed on May 13, 2014, provisional application No. 62/067,363, filed on Oct. 22, 2014.

(51) Int. Cl.
| | | |
|---|---|---|
| A61K 31/05 | (2006.01) | |
| A61K 9/00 | (2006.01) | |
| A61K 31/352 | (2006.01) | |
| B65D 25/08 | (2006.01) | |
| A23L 2/52 | (2006.01) | |
| B65D 1/02 | (2006.01) | |
| B65D 41/32 | (2006.01) | |
| B65D 17/28 | (2006.01) | |
| B65D 81/00 | (2006.01) | |

(52) U.S. Cl.
CPC .......... *A61K 31/352* (2013.01); *B65D 1/0246* (2013.01); *B65D 17/4012* (2018.01); *B65D 25/08* (2013.01); *B65D 41/32* (2013.01); *B65D 41/505* (2013.01); *B65D 81/3238* (2013.01); *B65D 81/3255* (2013.01); *A23V 2002/00* (2013.01); *B65D 2081/001* (2013.01)

(58) Field of Classification Search
CPC .............. B65D 17/4012; B65D 1/0246; A61K 31/352; A61K 9/0095; A61K 31/05; A23L 2/52–2/68; A23V 2002/00
USPC .................................. 426/115, 119–120, 394
See application file for complete search history.

(56) References Cited

U.S. PATENT DOCUMENTS

| | | | | |
|---|---|---|---|---|
| 4,221,291 A * | 9/1980 | Hunt | ................. | B65D 51/2842 |
| | | | | 206/222 |
| 4,319,614 A * | 3/1982 | Boice | ..................... | A47G 19/12 |
| | | | | 141/381 |
| 5,772,017 A * | 6/1998 | Kang | ................. | B65D 51/2842 |
| | | | | 206/222 |
| 5,950,819 A * | 9/1999 | Sellars | ............... | B65D 51/2885 |
| | | | | 206/221 |
| 5,980,959 A * | 11/1999 | Frutin | .................... | B65D 85/73 |
| | | | | 206/222 |
| 6,230,937 B1 * | 5/2001 | Johnson | ................. | B65D 49/04 |
| | | | | 222/147 |
| 6,372,270 B1 * | 4/2002 | Denny | .................... | A47G 19/22 |
| | | | | 206/219 |
| 6,527,110 B2 * | 3/2003 | Moscovitz | ......... | B65D 51/2835 |
| | | | | 206/222 |
| 6,705,462 B2 * | 3/2004 | Kasuya | .................. | B65D 25/08 |
| | | | | 206/222 |
| 6,786,330 B2 * | 9/2004 | Mollstam | ........... | B65D 47/2031 |
| | | | | 206/219 |
| 7,055,685 B1 * | 6/2006 | Patterson | ........... | B65D 51/2892 |
| | | | | 206/219 |
| 7,562,782 B2 * | 7/2009 | Yorita | ................ | B65D 51/2842 |
| | | | | 206/222 |
| 7,607,549 B2 * | 10/2009 | Morini | ............... | B65D 41/3438 |
| | | | | 206/219 |
| 7,886,899 B2 * | 2/2011 | Frutin | ................ | B65D 51/2892 |
| | | | | 206/221 |
| 9,480,647 B2 * | 11/2016 | Benson | ................. | A61J 1/1443 |
| 2004/0069148 A1 * | 4/2004 | Fenaroli | ................. | A47G 19/16 |
| | | | | 99/275 |
| 2006/0039959 A1 * | 2/2006 | Wessling | ............... | A61K 9/006 |
| | | | | 424/448 |
| 2008/0073307 A1 * | 3/2008 | Sweeney | ............ | B65D 51/2864 |
| | | | | 215/228 |
| 2008/0241339 A1 * | 10/2008 | Mitchell | ................ | A23L 2/385 |
| | | | | 426/598 |
| 2011/0303561 A1 * | 12/2011 | Zheng | ................... | B01F 13/002 |
| | | | | 206/219 |
| 2014/0001064 A1 * | 1/2014 | Aloia | ................. | B65D 81/3211 |
| | | | | 206/221 |
| 2014/0166157 A1 * | 6/2014 | Salinas | ............... | B65D 51/2835 |
| | | | | 141/329 |
| 2018/0009601 A1 * | 1/2018 | Byun | ........................ | A23F 3/34 |

* cited by examiner

1100

1102 Provide a beverage container separately storing an aqueous beverage and one or more polymer matrices that include cannabinoid compounds without exposing the one or more polymer matrices to the aqueous beverage, the beverage container including a closure that prevents egress, from the beverage container, of the aqueous beverage or the one or more polymer matrices stored in the beverage container

1104 The aqueous beverage is stored in a first reservoir in the beverage container, the first reservoir being configured to allow egress, from the first reservoir, of the aqueous beverage in the first reservoir subsequent to the closure being opened. The one or more polymer matrices are stored in a second reservoir, distinct from the first reservoir, in the beverage container, the second reservoir being configured to allow release of the one or more polymer matrices, from the second reservoir, into the aqueous beverage subsequent to the closure being opened.

1106 The cannabinoid compounds include one or more of: tetrahydrocannabinolic acid, tetrahydrocannabinol, and cannabidiol

1108 Release the one or more polymer matrices to the aqueous beverage by opening the closure

1110 The closure is opened within a predefined time before consumption of the cannabinoid compounds

1112 The predefined time is one of: one day, twelve hours, six hours, three hours, two hours, one hour, thirty minutes, and fifteen minutes

1114 A potency of the cannabinoid compounds decreases over time subsequent to releasing the cannabinoid compounds into the aqueous beverage

Figure 11

PREPARING BEVERAGES CONTAINING CANNABINOIDS USING BEVERAGE CONTAINERS WITH POLYMER MATRICES

CROSS REFERENCE TO RELATED APPLICATIONS

This application is a United States National Stage Application filed under 35 U.S.C. § 371 of PCT Patent Application Serial No. PCT/US2015/026710 filed on Apr. 20, 2015, which claims the benefit of and priority to U.S. Provisional Patent Application No. 61/982,278, filed on Apr. 21, 2014, U.S. Provisional Patent Application No. 61/992,745, filed on May 13, 2014, and U.S. Provisional Patent Application No. 62/067,363, filed on Oct. 22, 2014, which are hereby incorporated by reference in their entirety.

TECHNICAL FIELD

This application relates to the field of beverage containers, and particularly to beverage containers with water soluble cannabinoids.

BACKGROUND

Cannabinoids generally refer to chemical compounds that act on cannabinoid receptors on cells. Cannabinoids include cannabinoids derived from *cannabis*, such as tetrahydrocannabinol, cannabidiol, cannabinol, cannabigerol, tetrahydrocannabivarin, cannabidivarin, and cannabichromene. Cannabinoids also include cannabinoids derived from other plants. Cannabinoids further include synthetic cannabinoids.

Cannabinoids are often used for medical or recreational purposes. Cannabinoids can be administered by various methods, such as oral ingestion, smoking, vaporizing, etc.

SUMMARY

Cannabinoids are generally insoluble in water, and thus, are often extracted and stored in oil-based media (e.g., oil solution or oil-containing powder). Because hydrophobicity of oil-based media and insolubility of cannabinoids hinder interaction of the cannabinoids in oil-based media with aqueous solutions, it was believed that cannabinoids in an oil-based medium would retain their potency even if the oil-based medium is mixed with an aqueous solution.

The inventors of this application have found that, surprisingly, when cannabinoids are mixed with aqueous solution, a potency of the cannabinoids decreases significantly over time. Thus, beverages (e.g., aqueous beverage) containing cannabinoids cannot be stored for long without losing the potency of cannabinoids.

A number of embodiments that overcome the limitations and disadvantages described above are presented in more detail below. These embodiments provide beverage containers and methods described herein. By storing both a beverage (e.g., a non-cannabinoid beverage, which does not include cannabinoids) and cannabinoid compounds separately within a sealed beverage container and mixing the beverage and the cannabinoid compounds only within a certain time before consumption, the loss of potency is reduced. Such beverage containers provide additional benefits, such as storing cannabinoid compounds safely in a sealed environment so that the cannabinoid compounds are not accidentally released. In addition, the beverage containers described herein provide a simplified mechanism for mixing beverages and cannabinoid compounds, thereby facilitating preparation of beverages containing cannabinoids.

The inventors of this application have also found that cannabinoid compounds do not mix with well with an aqueous beverage due to the hydrophobicity of the oil-based media and insolubility of the cannabinoid compounds in water. Thus, releasing cannabinoid compounds into an aqueous beverage leads to a non-homogeneous mixture of cannabinoid compounds and the aqueous beverage (e.g., the oil-based media including cannabinoid compounds floating on the aqueous beverage), which results in a non-uniform rate of taking in cannabinoid compounds while drinking the aqueous beverage and reduced consumer satisfaction. As described below, the cannabinoid compounds included in one or more polymer matrices are used to address this problem. For example, the one or more polymer matrices are used to improve the solubility of the cannabinoid compounds or at least create a more homogeneous mixture of cannabinoid compounds and the aqueous beverage. The one or more polymer matrices also facilitate maintaining the potency of cannabinoid compounds while stored separately from the aqueous beverage.

In accordance with some embodiments, a beverage container for preparing a beverage containing cannabinoids includes a hollow container with a first reservoir and a second reservoir distinct from the first reservoir, both the first reservoir and the second reservoir positioned within the hollow container, the first reservoir configured to store an aqueous beverage, the second reservoir sealingly storing one or more polymer matrices that include cannabinoid compounds, the second reservoir preventing an exposure of the cannabinoid compounds to the aqueous beverage prior to the second reservoir being opened, the second reservoir being configured to release the one or more polymer matrices stored in the second reservoir into the aqueous beverage subsequent to the second reservoir being opened, the hollow container defining an opening through which a liquid in the hollow container is allowed to egress from the hollow container. The beverage container also includes a closure sealingly and operably coupled with the opening of the hollow container, the closure operably coupled with the second reservoir such that opening of the closure initiates opening of the second reservoir, the closure sealing the opening of the hollow container and preventing egress, from the hollow container, of the aqueous beverage or the one or more polymer matrices stored in the hollow container prior to the closure being opened, the closure allowing egress of the aqueous beverage and the cannabinoid compounds subsequent to the closure being opened.

In accordance with some embodiments, a method for preparing a beverage containing cannabinoids includes providing any beverage container described herein, and opening the closure of the beverage container and releasing the one or more polymer matrices to the aqueous beverage.

In accordance with some embodiments, a method for preparing a beverage containing cannabinoids includes providing a beverage container separately storing an aqueous beverage and one or more polymer matrices that include cannabinoid compounds without exposing the one or more polymer matrices to the aqueous beverage, the beverage container including a closure that prevents egress, from the beverage container, of the aqueous beverage or the one or more polymer matrices stored in the beverage container. The method also includes releasing the one or more polymer matrices to the aqueous beverage by opening the closure.

BRIEF DESCRIPTION OF THE DRAWINGS

For a better understanding of the aforementioned aspects as well as additional aspects and embodiments thereof, reference should be made to the Description of Embodiments below, in conjunction with the following drawings.

FIG. 11 is a flowchart illustrating a method for preparing a beverage containing cannabinoids in accordance with some embodiments.

Like reference numerals refer to corresponding parts throughout the drawings.

DESCRIPTION OF EMBODIMENTS

Beverage container and methods for preparing a beverage containing cannabinoids are described. Reference will be made to certain embodiments, examples of which are illustrated in the accompanying drawings. While the embodiments are described in conjunction with the drawings, it will be understood that it is not intended to limit the scope of the claims to these particular embodiments alone.

Reference will now be made in detail to embodiments, examples of which are illustrated in the accompanying drawing. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

Figure 1A:
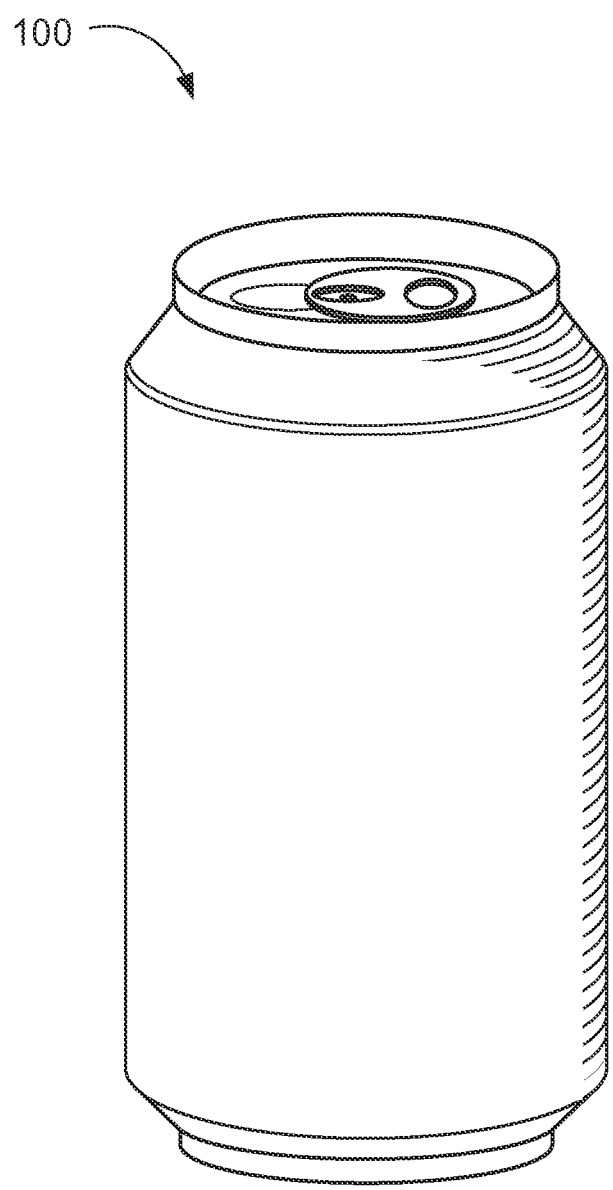
FIG. 1A is a perspective view of a beverage container in accordance with some embodiments.

FIG. 1A is a perspective view of a beverage container 100 in accordance with some embodiments.

The beverage container 100 shown in FIG. 1A is called a canister or a can. As shown in FIG. 1A, the can has a substantially cylindrical shape. For example, the can shown in FIG. 1A has a cylindrical portion between the top surface and the bottom surface. In some embodiments, the can is a cylindrical receptacle.

In some embodiments, the can is made of metal (e.g., aluminum). In some embodiments, the can is made primarily of aluminum (e.g., aluminum alloy). In some embodiments, the can is made of plastic. In some embodiments, the can is made of glass (e.g., a glass body with an aluminum lid). In some embodiments, the can includes plastic. In some embodiments, the can includes glass.

Figure 1B:
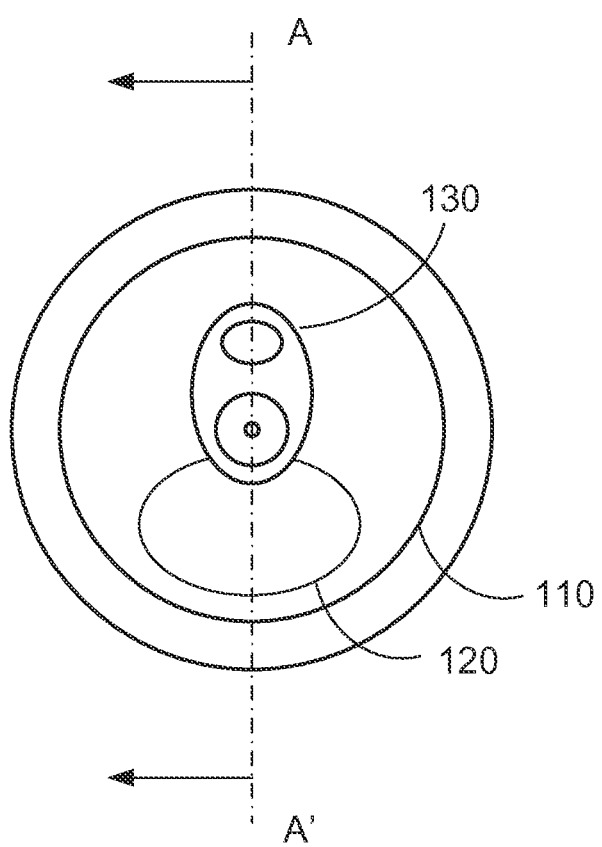
FIG. 1B is a top view of the beverage container shown in FIG. 1A in accordance with some embodiments.

FIG. 1B is a top view of the can shown in FIG. 1A in accordance with some embodiments. FIG. 1B shows a lid 110 of the can. In some embodiments, the lid 110 refers to a generally planar surface on top of the can. As used herein, an inner surface of the lid 110 is called a top surface. As used herein, an inner surface of a bottom lid is called a bottom surface.

In some embodiments, an opening 120 is defined by one or more grooves in the lid 110 of the hollow container. In some embodiments, the one or more grooves are formed by scoring the lid of the hollow container.

FIG. 1B also shows a tab 130 (e.g., a stay-on tab). When opening the can, the tab 130 operates as a lever. Pulling a distal end of the tab 130 (e.g., an end of the tab 130 that is further away from the opening) upward moves a proximal end of the tab 130 (e.g., an end of the tab 130 that is proximate to the opening), that is opposite from the distal end of the tab 130, toward the opening, thereby depressing and opening the scored portion of the lid 110.

Figure 2C:
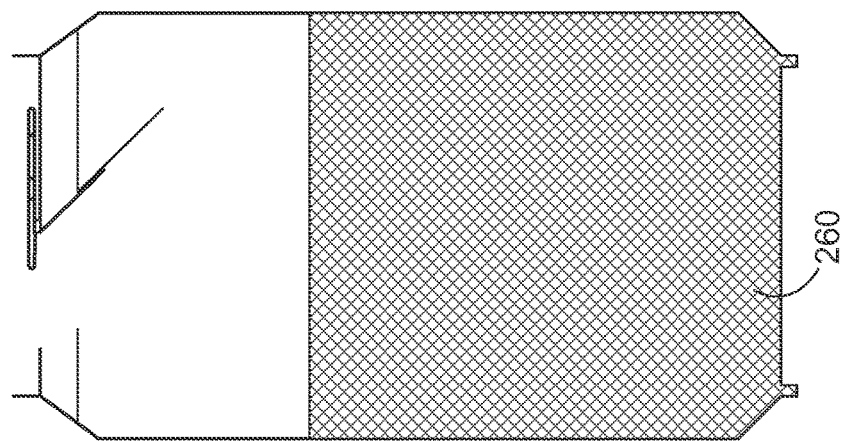
FIGS. 2A-2C are schematic diagrams illustrating operations of a beverage container in accordance with some embodiments.
Figure 2B:
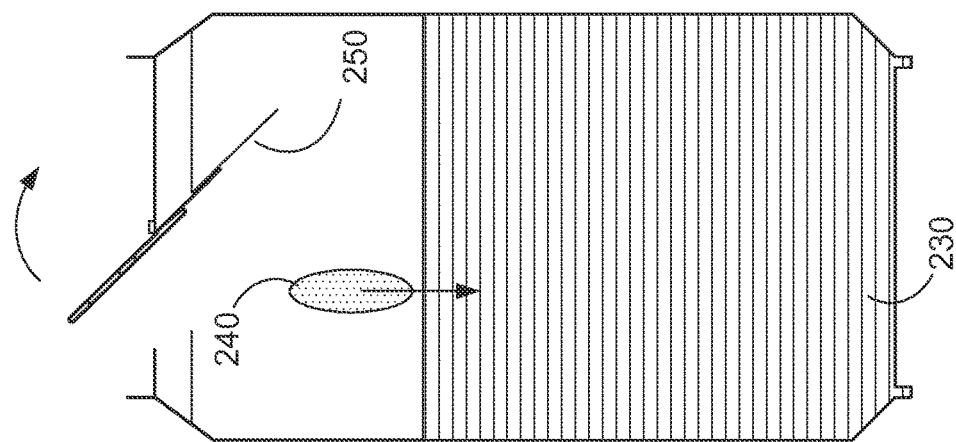
Figure 2A:
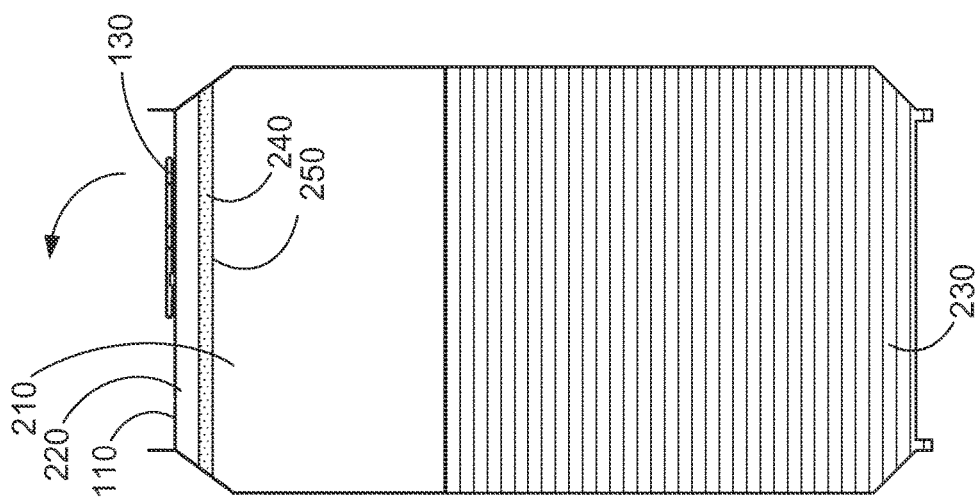

FIG. 1B indicates plane AA' upon which views illustrated in FIGS. 2A-2C are taken.

FIGS. 2A-2C are schematic diagrams illustrating operations of a beverage container in accordance with some embodiments.

FIG. 2A shows a cross-section of the can shown in FIG. 1A in accordance with some embodiments. Within the can, a first reservoir 210 and a second reservoir 220 are defined. The first reservoir 210 is sealed from the second reservoir 220 so that a liquid (or a substance in any other form, such as solid) in the second reservoir 220 cannot enter the first reservoir 210 until the first reservoir 210 is opened. Similarly, the second reservoir 220 is sealed from the first reservoir 210 so that a liquid in the first reservoir 210 cannot enter the second reservoir 220 until the second reservoir is opened. In some embodiments, as shown in FIG. 2A, the first reservoir and the second reservoir are separated by a separation layer 250. In some embodiments, the separation layer 250 is made of metal (e.g., aluminum). In some embodiments, the separation layer 250 is made of plastic. In some embodiments, the separation layer 250 is made of a material that is configured for puncturing or tearing. For example, in some embodiments, the separation layer 250 is a wax paper.

FIG. 2A also shows that the first reservoir 210 stores an aqueous beverage 230 (e.g., still or sparkling, flavored or non-flavored, etc.), and the second reservoir 220 stores a one or more polymer matrices 240. In some embodiments, the one or more polymer matrices 240 include cannabinoid compounds. In some embodiments, the second reservoir 220 stores two or more types of distinct polymer matrices. In some embodiments, a first polymer matrix of the two or more types of distinct polymer matrices includes cannabinoid compounds of a first type, and a second polymer matrix of the two or more types of distinct polymer matrices includes cannabinoid compounds of a second type that is distinct from cannabinoid compounds of the first type. In some embodiments, the first polymer matrix and the second polymer matrix of the two or more types of distinct polymer matrices include cannabinoid compounds of a same type. In some embodiments, the first polymer matrix of the two or more types of distinct polymer matrices includes a polymer of a first type, and the second polymer matrix of the two or more types of distinct polymer matrices includes a polymer of a second type that is distinct from the polymer of the first type. In some embodiments, the first polymer matrix and the second polymer matrix of the two or more types of distinct polymer matrices include a polymer of a same type.

Pulling the distal end of the tab 130 opens the lid 110 as described above with respect to FIG. 1B. While the distal end of the tab 130 is being pulled, a portion of the lid 110 that is depressed by the proximal end of the tab 130 continues to move downward toward the separation layer 250, depresses the separation layer 250, and breaks at least a portion of the separation layer 250, as shown in FIG. 2B. Breaking the separation layer 250 releases the one or more polymer matrices 240 that were stored in the second reservoir 220 to the aqueous beverage 230 stored in the first reservoir 210.

FIG. 2C shows that the distal end of the tab 130 is pulled back (e.g., for consuming the beverage inside the can) and the one or more polymer matrices 240 are mixed with the aqueous beverage 230. Cannabinoid compounds in the one or more polymer matrices 240 are released into the aqueous beverage 230, thereby forming a cannabinoid beverage 260.

In some embodiments, the separation layer 250 is substantially flat. In some embodiments, the separation layer 250 is curved or indented. For example, in some embodiments, the separation layer 250 is concaved to facilitate a release of the one or more polymer matrices 240.

In some embodiments, the separation layer 250 has an opening defined by one or more grooves in the separation layer 250. In some embodiments, the one or more grooves are formed by scoring the separation layer 250. The scored portion of the separation layer 250 facilitates breaking or opening the separation layer 250.

Figure 3A:
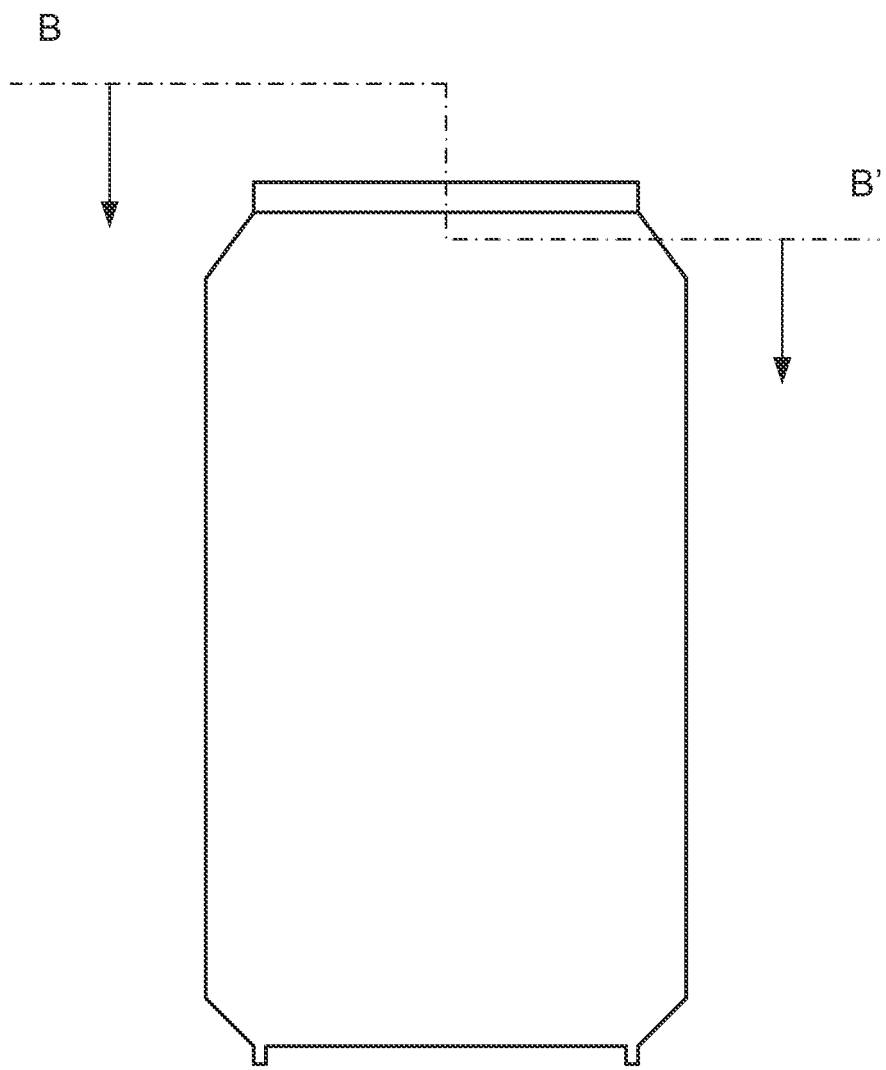
FIG. 3A is a front view of a beverage container in accordance with some embodiments.

FIG. 3A is a front view of a beverage container in accordance with some embodiments. In FIG. 3A, plane BB' are indicated upon which views illustrated in FIGS. 3B-3E are taken.

FIGS. 3B-3E are partial cross sectional views of a beverage container in accordance with some embodiments. FIGS. 3B-3E show that the separation layer 250 has an opening.

Figure 3B:
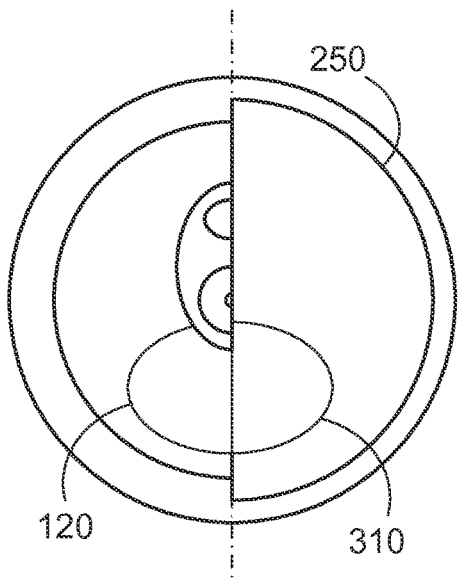
FIGS. 3B-3E are partial cross sectional views of a beverage container in accordance with some embodiments.

FIG. 3B shows that, in some embodiments, the opening 310 of the separation layer 250 is aligned with the opening 120 of the lid. In some embodiments, the opening 310 of the separation layer 250 is located on a same side as the opening 120 on the lid. For example, as shown in FIG. 3B, the opening 120 is located on a proximal half of the lid (e.g., a lower half of the lid), and the opening 320 is also located on a proximal half of the separation layer 250 (e.g., a lower half of the separation layer 250).

Figure 3C:
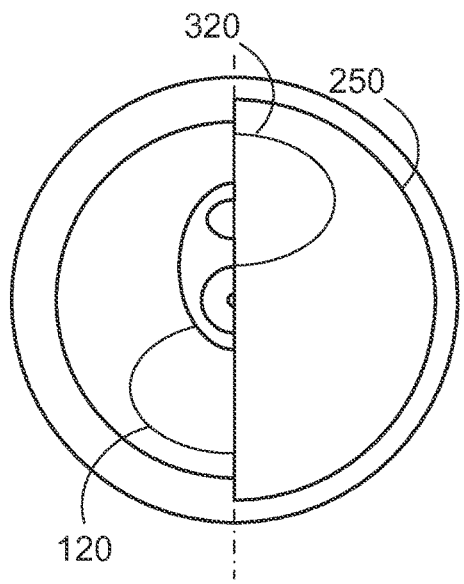

FIG. 3C shows that, in some embodiments, the opening 320 of the separation layer 250 is located on a side opposite to a side of the opening 120 on the lid. For example, as shown in FIG. 3C, the opening 120 is located on a proximal half of the lid (e.g., a lower half of the lid), and the opening 320 is located on a distal half of the separation layer 250 (e.g., an upper half of the separation layer 250).

Figure 3D:
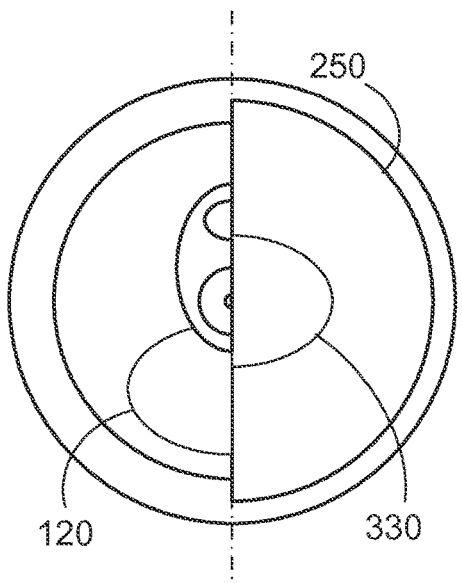

FIG. 3D shows that, in some embodiments, the opening 330 of the separation layer 250 is located in a middle of the separation layer 250.

Figure 3E:
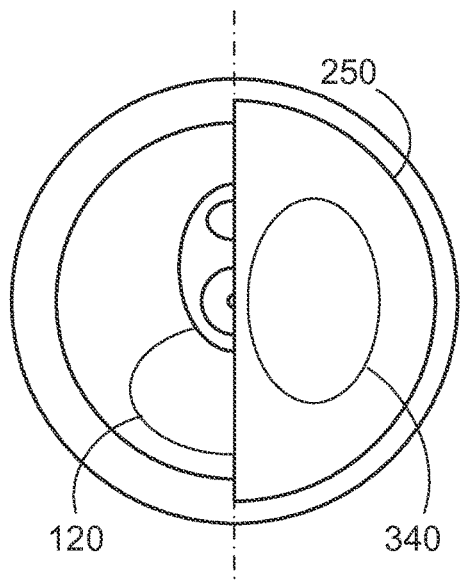

FIG. 3E shows that, in some embodiments, the opening 340 of the separation layer 250 is located on a side of the separation layer 250 (e.g., a direction from a center of the separation layer 250 to the opening 340 of the separation layer 250 is perpendicular to a direction from a center of the lid to the opening 120 of the lid).

In some embodiments, multiple openings are defined in the separation layer 250.

Figure 4C:
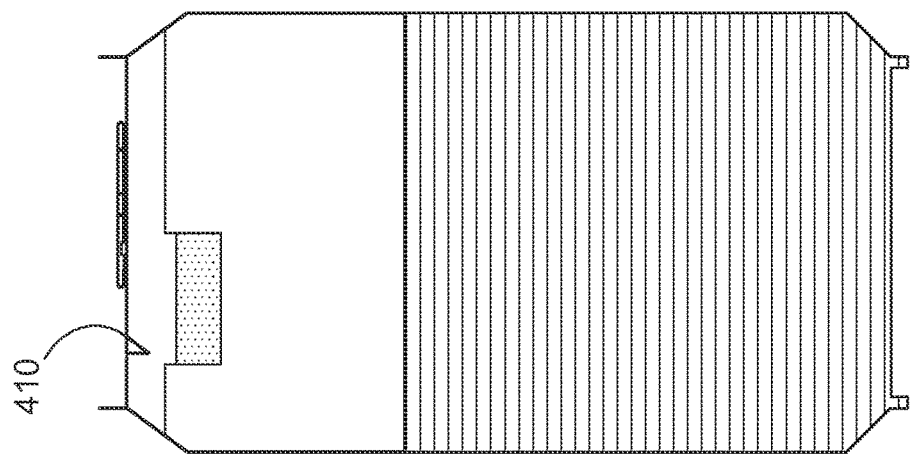
FIGS. 4A-4C are schematic diagrams illustrating a beverage container in accordance with some embodiments.
Figure 4B:
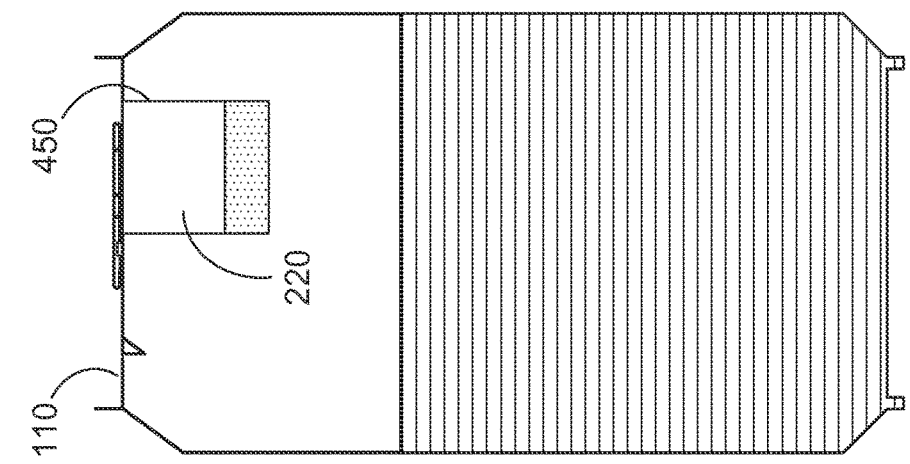
Figure 4A:
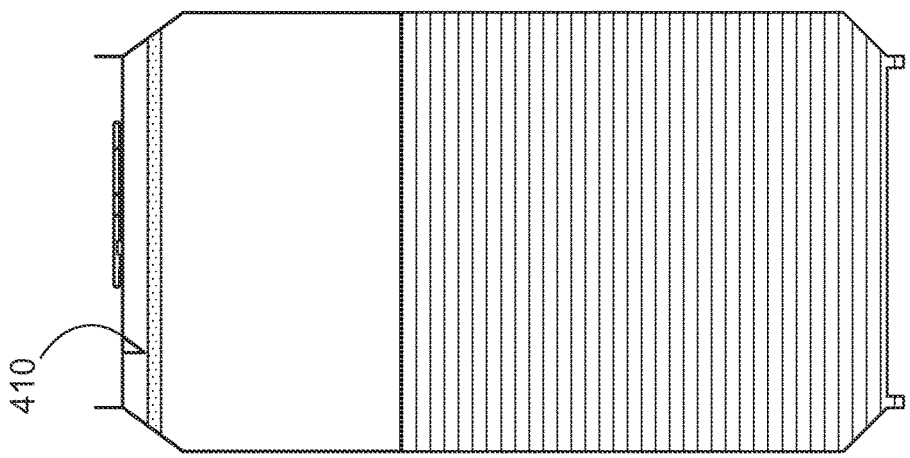

FIGS. 4A-4C are schematic diagrams illustrating a beverage container in accordance with some embodiments.

FIG. 4A shows that, in some embodiments, the beverage container includes a puncturing device 410. The puncturing device 410 typically includes a pointy tip, a sharp edge, or a serrated edge to facilitate breaking the separation layer. In some embodiments, the puncturing device 410 has a round tip to facilitate pressing an opening on the separation layer. In some embodiments, the rounded tip is formed by forming an indentation on the lid (e.g., by pressing the lid with a mold).

FIG. 4B shows that the separation layer need not be flat and that the separation layer need not extend wall-to-wall. As shown in FIG. 4B, in some embodiments, the separation layer has a shape of a cup (sealed side walls and a bottom surface) that is sealingly attached to the lid 110. With the beverage container shown in FIG. 4B, opening the lid 110 initiates puncturing the separation layer 450 with the puncturing device 410, thereby opening the second reservoir 220.

FIG. 4C shows that the separation layer has an indentation. In some embodiments, one or more polymer matrices that include cannabinoid compounds are placed within the indentation. This allows the one or more polymer matrices to be placed in an area smaller than an entire separation layer surface, thereby facilitating release of the one or more polymer matrices when the separation layer is opened.

Figure 5C:
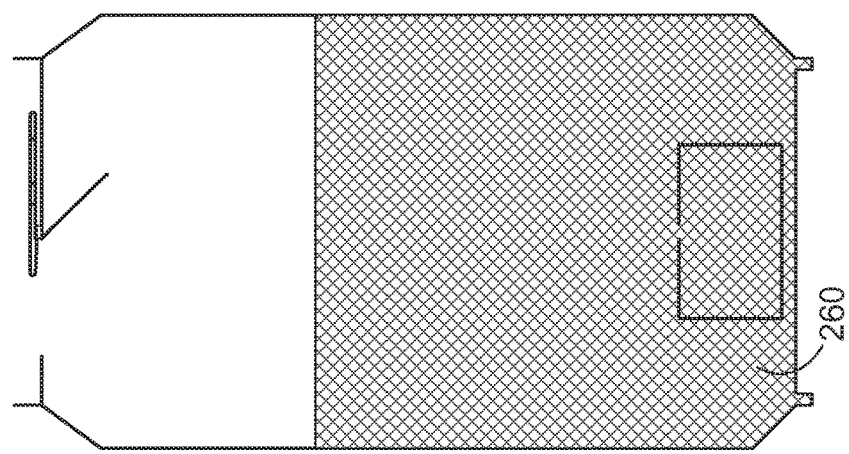
FIGS. 5A-5C are schematic diagrams illustrating operations of a beverage container in accordance with some embodiments.
Figure 5B:
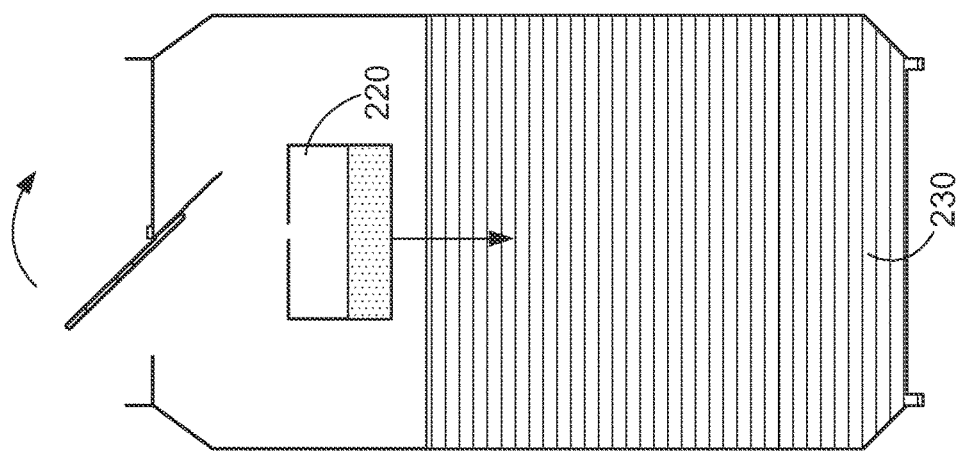
Figure 5A:
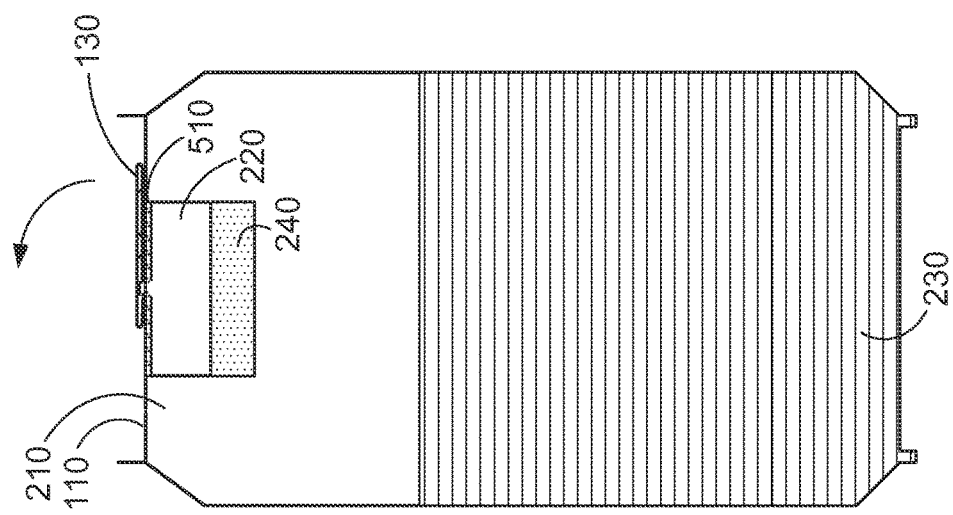

FIGS. 5A-5C are schematic diagrams illustrating operations of a beverage container in accordance with some embodiments.

FIG. 5A illustrates that the second reservoir 220 is releasably attached to the lid 110 (e.g., using an adhesive 510 or with a mechanical mechanism, such as a latch). The second reservoir 220 is manufactured as a separate reservoir with an opening. The second reservoir 220 is sealingly attached to the lid 110 so that a liquid (or cannabinoid compounds in any other form) in the second reservoir 220 does not egress from the second reservoir 220 while the second reservoir 220 is attached to the lid 110. For example, the adhesive 510 serves as a water-proof seal while the opening of the second reservoir 220 is fully covered by the adhesive 510.

FIG. 5B illustrates that pulling the distal end of the tab 130 opens the lid 110 as described above with respect to FIG. 1B. While the distal end of the tab 130 is being pulled, a portion of the lid 110 that is depressed by the proximal end of the tab 130 continues to move downward, pushing the second reservoir 220 away from the lid 110. As a result, the second reservoir 220 is detached from the lid 110.

FIG. 5C illustrates that once the second reservoir 220 is released into the aqueous beverage 230, the aqueous beverage 230 in the first reservoir 210 enters the second reservoir 220, mixing with the one or more polymer matrices in the second reservoir 220. The one or more polymer matrices release cannabinoid compounds into the aqueous beverage 230, forming a cannabinoid beverage 260.

In some embodiments, the can has a twist-and-shut mechanism, which is illustrated in FIGS. 6A-6D.

Figure 6A:
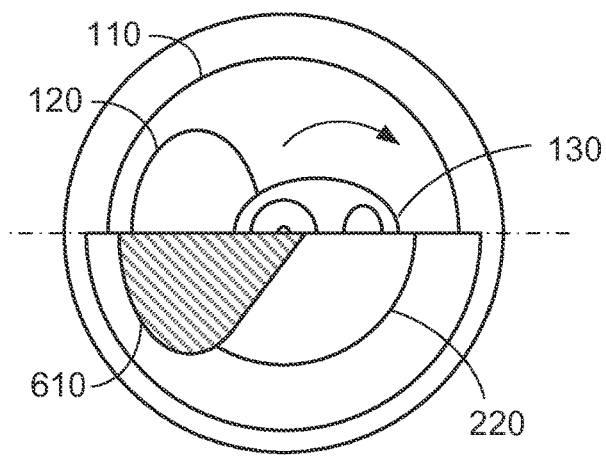
FIG. 6A is a partial cross sectional view of a beverage container in a closed configuration in accordance with some embodiments.

FIG. 6A is a partial cross-sectional top view of a beverage container in a closed configuration in accordance with some embodiments.

A top-half of FIG. 6A illustrates a plain top view of the beverage container. A bottom-half of FIG. 6A illustrates a cross-sectional view of the beverage container along a plane perpendicular to, and immediately under, the lid 110.

In FIG. 6A, the opening 120 is sealed by a flap 610 located inside the beverage container. In some embodiments, the flap 610 is made of plastic. In some embodiments, the flap 610 is made of metal. In some embodiments, the flap 610 is made of rubber.

The flap 610 is mechanically coupled with the tab 130, such that rotating the tab 130 also rotates the flap 610.

Figure 6B:
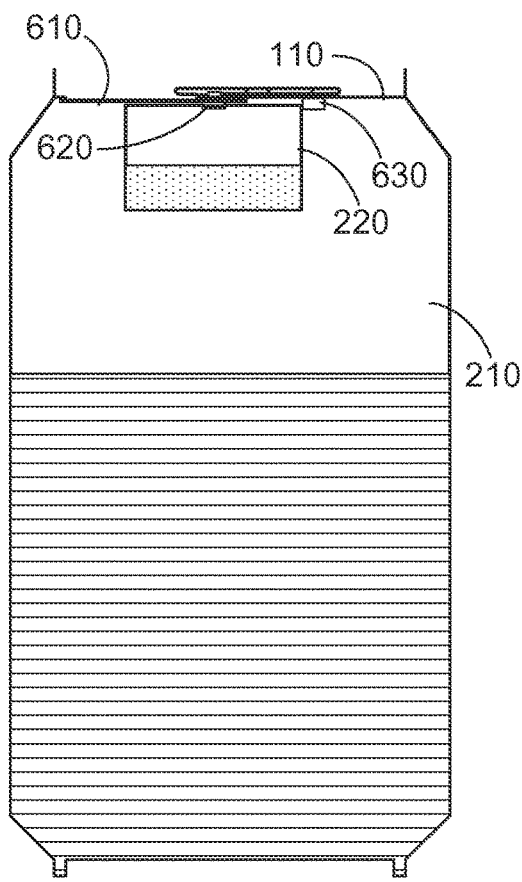
FIG. 6B is a schematic diagram illustrating an inner structure of the beverage container shown in FIG. 6A in accordance with some embodiments.

FIG. 6B is a schematic diagram illustrating an inner structure of the beverage container shown in FIG. 6A in accordance with some embodiments.

FIG. 6B shows that the second reservoir 220 is attached to the lid 110 with a mechanical holder 620. In some embodiments, the mechanical holder 620 is threaded (e.g., a screw), and an inner surface of an opening of the second reservoir 220 is also threaded. In some embodiments, the opening of the second reservoir 220 is slotted and the mechanical holder 620 is a clamp with an elongated end configured to mate with the slotted opening of the second reservoir 220. When the slotted opening and the elongated end are positioned perpendicular to each other, the second reservoir 220 is held by the elongated end. When the slotted opening and the elongated end are positioned in parallel, the second reservoir 220 is released by the elongated end.

Figure 6C:
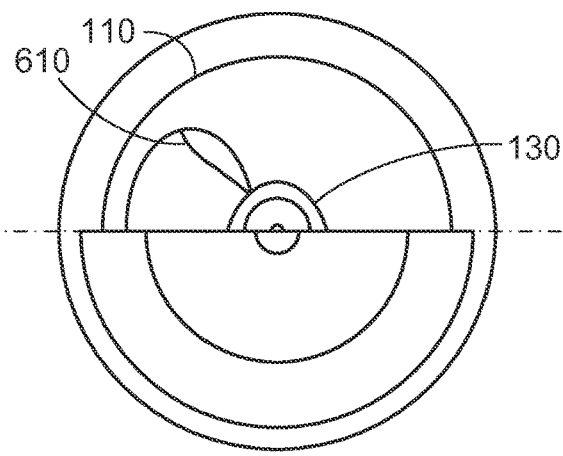
FIG. 6C is a partial cross sectional view of the beverage container, shown in FIG. 6A, in an open configuration in accordance with some embodiments.

FIG. 6C is a partial cross sectional view of the beverage container, shown in FIG. 6A, in an open configuration in accordance with some embodiments.

Again, a top-half of FIG. 6C illustrates a plain top view of the beverage container. A bottom-half of FIG. 6C illustrates a cross-sectional view of the beverage container along a plane perpendicular to, and immediately under, the lid 110.

Compared to FIG. 6A, the tab 130 and the flap 610 in FIG. 6C have been rotated, thereby opening the beverage container.

Figure 6D:
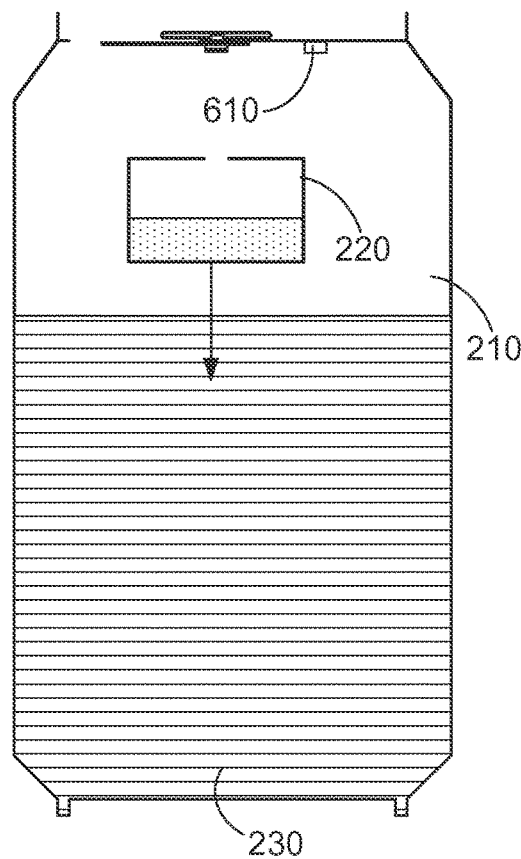
FIG. 6D is a schematic diagram illustrating an inner structure of the beverage container shown in FIG. 6C in accordance with some embodiments.

FIG. 6D is a schematic diagram illustrating an inner structure of the beverage container shown in FIG. 6C in accordance with some embodiments. FIG. 6D shows that the second reservoir 220 has been released.

Subsequent to the release of the second reservoir 220, the second reservoir 220 enters the aqueous beverage 230, and the aqueous beverage 230 in the first reservoir 210 enters the second reservoir 220, mixing with one or more polymer matrices stored in the second reservoir 220. The one or more polymer matrices release cannabinoid compounds into the aqueous beverage 230, forming a cannabinoid beverage 260. The entry of the second reservoir 220 into the aqueous beverage 230 is similar to the second reservoir 220 shown in FIG. 5C. For brevity, the description is not repeated herein.

Although FIGS. 6A-6D illustrate embodiments with the flap 610 located inside the beverage container, in some embodiments, different twist-and-shut mechanisms can be used. For example, the flap 610 may be located outside the beverage container so that it can be directly rotated. In some embodiments, a tab that covers a substantial portion of the lid 110 with a hole is used. A liquid inside the beverage container is allowed to egress from the beverage container when the hole in the tab is aligned with the opening in the lid 120, and the liquid inside the beverage container is prevented from egressing from the beverage container when the hole is not aligned with the opening in the lid 120.

Figure 7:
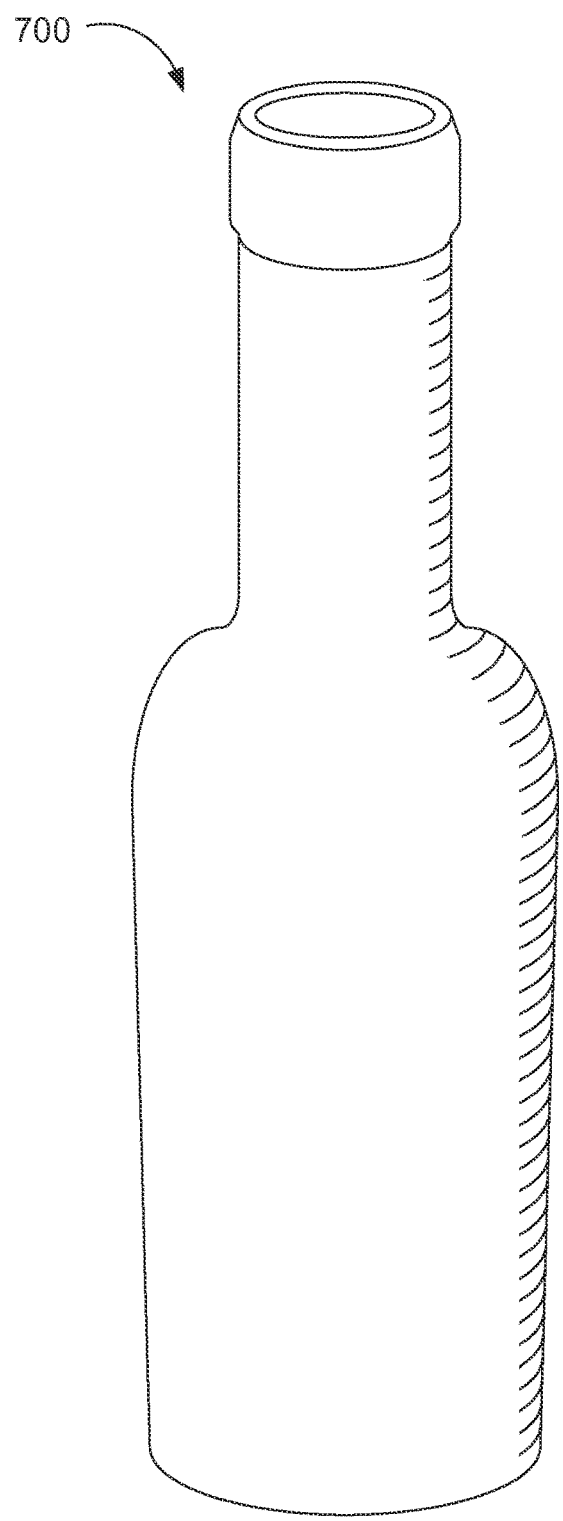
FIG. 7 is a perspective view of a beverage container in accordance with some embodiments.

FIG. 7 is a perspective view of a beverage container 700 in accordance with some embodiments. The beverage container 700 shown in FIG. 7 is called a bottle. As shown in FIG. 7, in some embodiments, the bottle is a receptacle with a neck adjacent to the opening of the beverage container and a body distinct from the neck, the neck of the beverage container having a diameter less than a diameter of the body (e.g., a diameter corresponding to a widest portion of the body) of the beverage container. In some embodiments, the body of the bottle has a substantially flat bottom. In some embodiments, the bottle has a substantially flat bottom. In some embodiments, the bottle has a bottom with its one or more edges defining a substantially flat surface (e.g., a middle portion of the bottom may be recessed, but an along a circumference of the bottom defines a substantially flat surface, allowing the bottom to stand on a flat surface, such as a table). In some embodiments, the bottom of the beverage container has a diameter that is less than the diameter of the body of the beverage container. In some embodiments, the diameter of the neck of the beverage container is less than the diameter of the bottom of the beverage container.

In some embodiments, the bottle is made of glass. In some embodiments, the bottle is made of plastic. In some embodiments, the bottle is made of metal (e.g., aluminum). In some embodiments, the bottle includes glass. In some embodiments, the bottle includes plastic. In some embodiments, the bottle includes metal.

FIGS. 8A-8E are partial cross-sectional views of the beverage container (e.g., including a bottle) shown in FIG. 7 in accordance with some embodiments. In particular, FIGS. 8A-8E show a portion of the beverage container, adjacent to an opening of the bottle and a cap 840 in accordance with some embodiments.

Figure 8B:
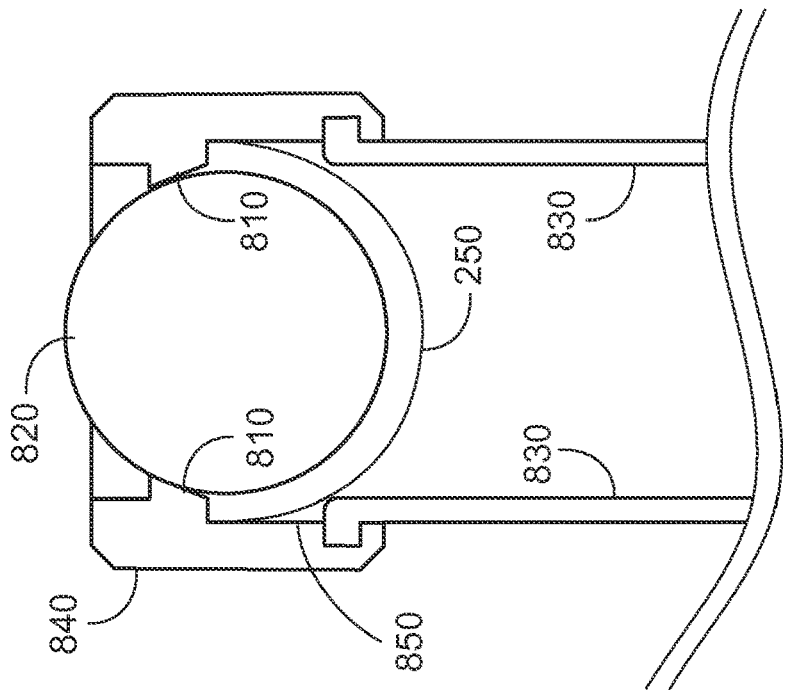
FIGS. 8A-8F are partial cross-sectional views of the beverage container shown in FIG. 7 in accordance with some embodiments.
Figure 8A:
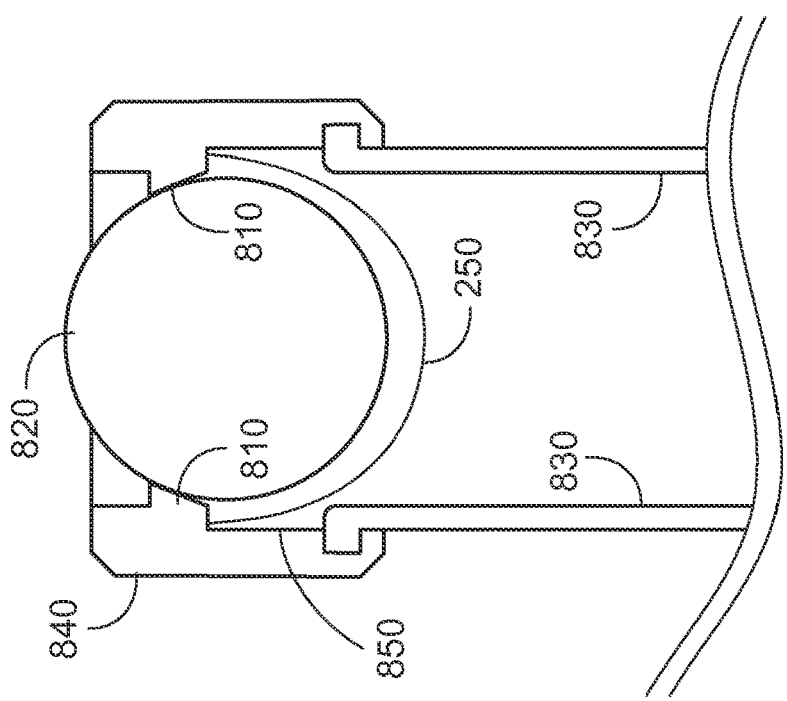

FIG. 8A shows an object (e.g., a sphere) 820 located at least partially within the cap 840. In some embodiments, the object 820 has a conical shape (e.g., a shape of a cone). In some embodiments, the object 820 has a shape of a conical frustum. The cap 840 also has one or more protrusions and/or indentations 810, which prevent egress of the object 820 from the beverage container. While the object 820 is positioned tightly against the one or more protrusions and/or indentations 810, a combination of the object 820 and the one or more protrusions and/or indentations 810 prevents an aqueous beverage or one or more polymer matrices (including cannabinoid compounds) stored in the beverage container from egressing from the beverage container. However, after the object 820 ceases to remain in contact with the one or more protrusions and/or indentations 810, the aqueous beverage or the one or more polymer matrices stored in the beverage container may egress from the beverage container (e.g., when the beverage container is tilted). The cap 840 has one or more inner surfaces (also called herein inner sidewalls 850 of the cap 840). The bottle also has one or more inner surfaces (also called herein inner sidewalls 830 of the bottle).

In FIG. 8A, a separation layer 250 is attached to the one or more protrusions and/or indentations 810. In some embodiments, the separation layer 250 is made of plastic (e.g., a plastic film). In some embodiments, the separation layer 250 is made of metal (e.g., aluminum).

In FIG. 8A, the object 820 (or at least a lower portion of the object 820), at least a portion of the one or more protrusions and/or indentations 810 (e.g., at least a lower portion of the one or more protrusions and/or indentations 810), and the separation layer 250 defines the second reservoir. The beverage container includes one or more polymer matrices, that include cannabinoid compounds, in the second reservoir. The one or more polymer matrices are omitted in FIGS. 8A-8C so as not to obscure the understanding of the drawings.

In some embodiments, a remaining closed space within the beverage container corresponds to the first reservoir. In some embodiments, the first reservoir is defined by the separation layer 250, at least a portion of the one or more inner sidewalls 850 of the cap 840, the one or more inner sidewalls 830 of the bottle, and a bottom surface (an inner surface of the bottom of the bottle). The first reservoir stores the aqueous beverage.

Figure 8C:
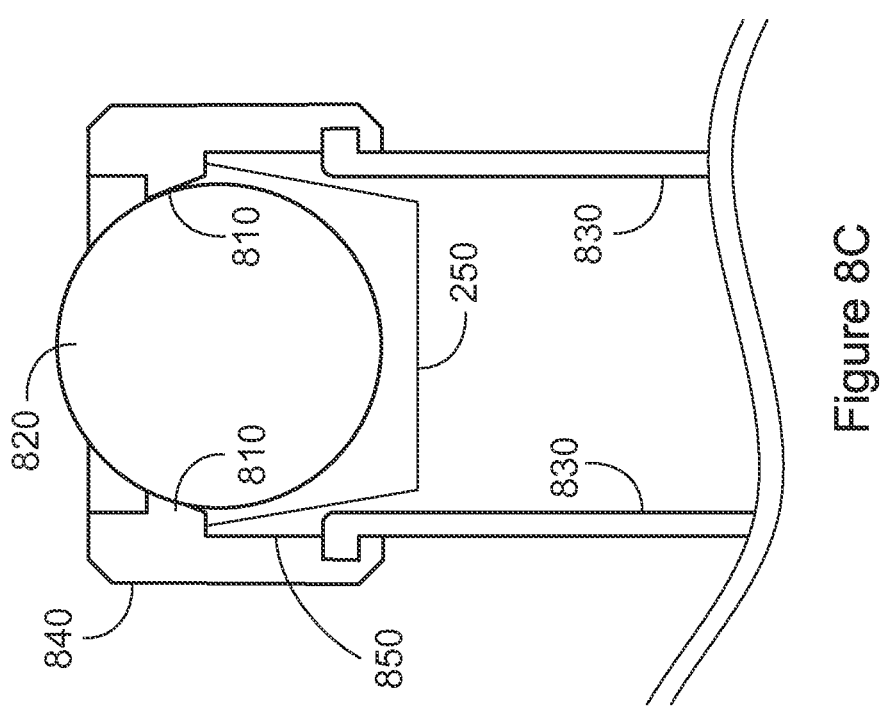

FIGS. 8B and 8C include many features of FIG. 8A, whose descriptions are not repeated herein for brevity.

FIG. 8B differs from FIG. 8A at least in that the separation layer 250 is attached to the one or more sidewalls 830, instead of the one or more protrusions and/or indentations 810.

FIG. 8C differs from FIG. 8A at least in that the separation layer 250 has a flat bottom surface.

The beverage container shown in FIGS. 8A-8C may be opened in a manner similar to a Codd-neck bottle. In some embodiments, the object 820 is pressed downward. In some embodiments, moving the object 820 down by more than a predefined distance breaks (e.g., tears) the separation layer 250, thereby releasing one or more polymer matrices, including cannabinoid compounds, stored in the second reservoir into the aqueous beverage stored in the beverage container. The one or more polymer matrices release the cannabinoid compounds into the aqueous beverage, thereby forming a cannabinoid beverage. After the separation layer 250 is broken, the object 820 also falls, thereby allowing liquid (e.g., the cannabinoid beverage) to egress from the beverage container. In some embodiments, the object 820 falls into the aqueous beverage stored in the beverage container. In some embodiments, the object 820 falls to a chamber formed in a neck of the bottle, the chamber configured for holding the object 820.

Figure 8D:
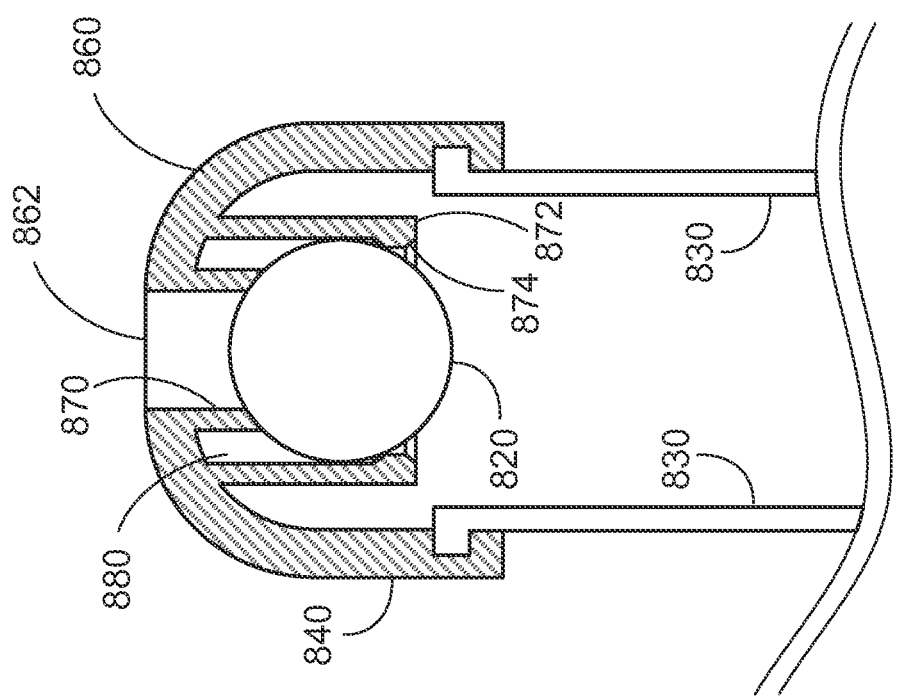
Figure 8E:
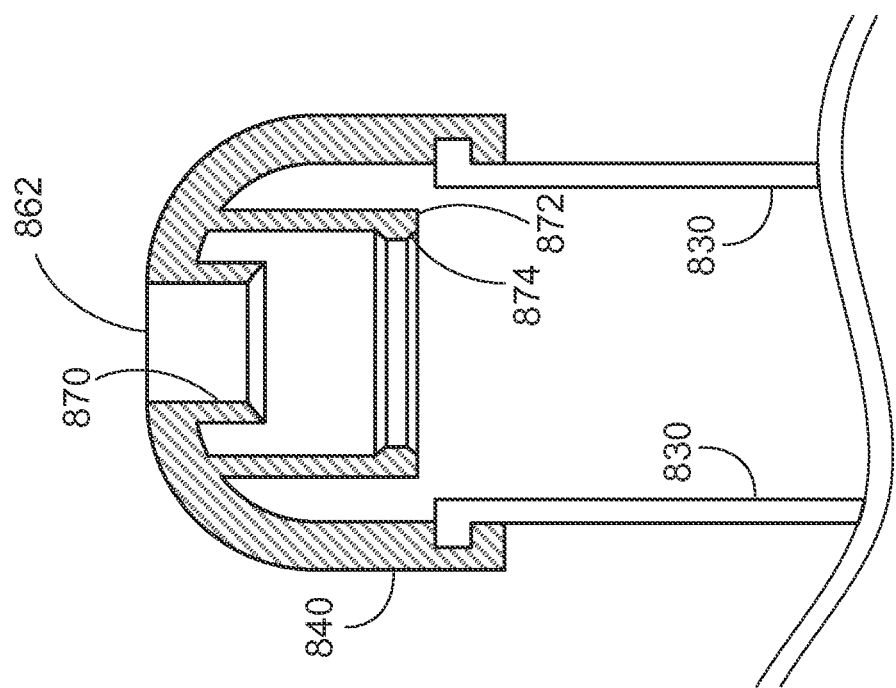
Figure 8F:
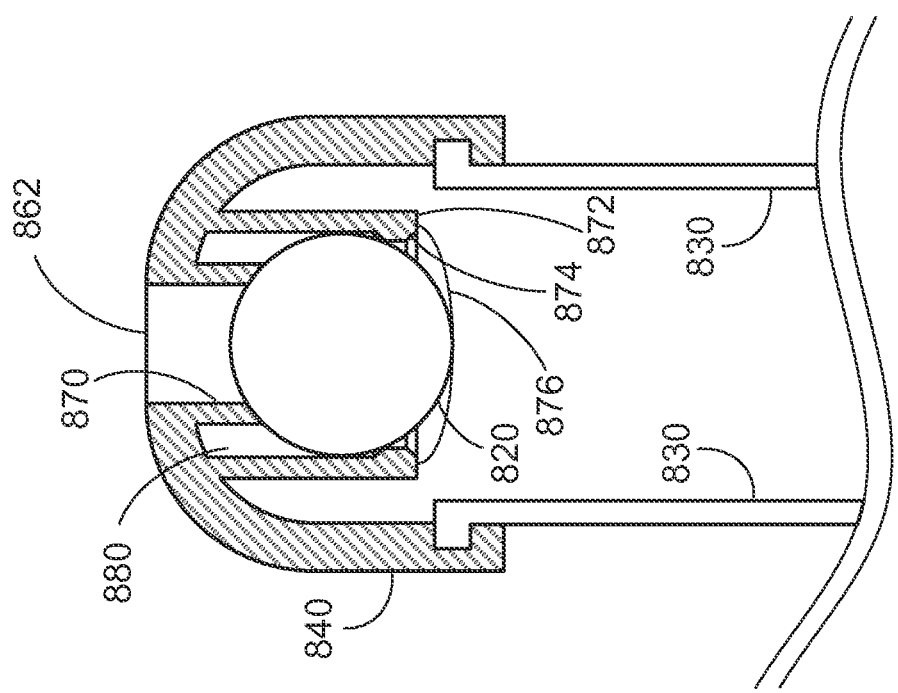

FIGS. 8D-8F are partial cross-sectional views of the beverage container (e.g., including a bottle) shown in FIG. 7 in accordance with some embodiments.

In FIG. 8D, the cap 840 defines a through hole 862. Once the closure is opened, the aqueous beverage (and cannabinoid compounds) can egress from the beverage container through the through hole 862. Although the through hole 862 is illustrated as a single hole in FIG. 8D, the cap 840 may define multiple through holes.

In FIG. 8D, the cap 840 has a first wall 870 and a second wall 872 on an inner surface of the cap 840. The first wall 870 has a first wall diameter and the second wall 872 has a second wall diameter larger than the first wall diameter. In some embodiments, each of the first wall and the second wall has a shape of a pipe of a respective diameter. In some embodiments, the first wall and/or the second wall have/has a shape of an expanding pipe (e.g., a diameter of the pipe increases or decreases toward the through hole 862). As used herein, a portion 860 of the cap 840 that is connected with, but is distinct from, the first wall 870 and the second wall 872 is called an outer layer 860. In some embodiments, the outer layer 860 of the cap 840 defines the through hole 862.

The cap 840 includes an object 820 (e.g., a sphere) at least partially located within the cap 840, adjacent to the opening of the hollow container, on an inner surface of the cap 840. In some embodiments, the object 820 has a diameter larger than the first wall diameter and smaller than the second wall diameter. The first wall prevents egress, from the beverage container, of the object 820 at least partially located within the cap 840.

The object 820 is sealingly positioned in contact with the first wall and the second wall, preventing egress, from the beverage container, of the aqueous beverage or the cannabinoid compounds (or the one or more polymer matrices containing the cannabinoid compounds) stored in the beverage container prior to the closure being opened.

The beverage container includes one or more inner sidewalls 830 of the bottle and an inner bottom surface of the bottle.

In FIG. 8D, the second reservoir 880 is located between at least a portion of the first wall 870 and at least a portion of the second wall 872. In some embodiments, the second reservoir 880 is defined at least by the object 820, at least a portion of the first wall 870, at least a portion of the second wall 872, and at least a portion of the outer layer 860 of the cap 840. In some embodiments, the second reservoir 880 is divided into multiple chambers. For example, the cap 840 may include a third wall between the first wall 870 and the second wall 872, providing a first chamber between the first wall 870 and the third wall and a second chamber between the second wall 872 and the third wall. In some embodiments, cannabinoid compounds are included in only a subset, less than all, of the chambers. For example, only one of the first chamber and the second chamber includes cannabinoid compounds. In some embodiments, all of the chambers include cannabinoid compounds. For example, each of the first chamber and the second chamber includes cannabinoid compounds.

The first reservoir is defined by the bottom surface of the bottle, at least a portion of the one or more inner sidewalls 830 of the bottle, and at least a portion of the cap 840 (e.g., at least a portion of the outer layer 860 of the cap 840 and at least a portion of the second wall 872 of the cap 840).

In some embodiments, the second wall 872 includes one or more protrusions and/or indentations 874 for releasably positioning the object 820 in contact with the first wall 870 and the second wall 872. For example, when the second wall 872 has a shape of a pipe, the one or more protrusions and/or indentations 874 may be a lip that extends toward a center of the pipe.

The beverage container shown in FIG. 8D also may be opened in a manner similar to a Codd-neck bottle. In some embodiments, the object 820 is pressed downward. In some embodiments, moving the object 820 down by more than a predefined distance breaks (e.g., tears) the separation layer 876, if present. Moving the object 820 down releases one or more polymer matrices, including cannabinoid compounds, stored in the second reservoir 880 into the aqueous beverage stored in the beverage container. The one or more polymer matrices release the cannabinoid compounds into the aqueous beverage, thereby forming a cannabinoid beverage. After the object 820 is released from the second wall 872, the object 820 also falls, thereby allowing liquid (e.g., the cannabinoid beverage) to egress from the beverage container. In some embodiments, the object 820 falls into the aqueous beverage stored in the beverage container. In some embodiments, the object 820 falls to a chamber formed in a neck of the bottle, the chamber configured for holding the object 820.

In FIG. 8E, the object 820 (shown in FIG. 8D) has been released from the second wall 872 and no longer prevents egress of the aqueous beverage (and cannabinoid compounds) from the beverage container through the through hole 862. Thus, the aqueous beverage (and cannabinoid compounds dissolved therein) can egress from the beverage container through the through hole 862.

FIG. 8F is similar to FIG. 8D except that the beverage container includes a separation layer 876. The optional separation layer 876 reduces unintended release of the aqueous beverage stored in the first reservoir. For example, the separation layer 876, in combination with the one or more protrusions and/or indentations 874, holds the object 820 against the first wall 870. In addition, the separation layer 876 reduces unintended release of the cannabinoid compounds stored in the second reservoir to the aqueous beverage stored in the first reservoir, until the separation layer 876 is opened. In some embodiments, the beverage container includes the separation layer 876 in lieu of the one or more protrusions and/or indentations 874 (shown in FIG. 8D), for holding the object 820. For example, the beverage container may include the separation layer 876 without the one or more protrusions and/or indentations 874.

Figure 9A:
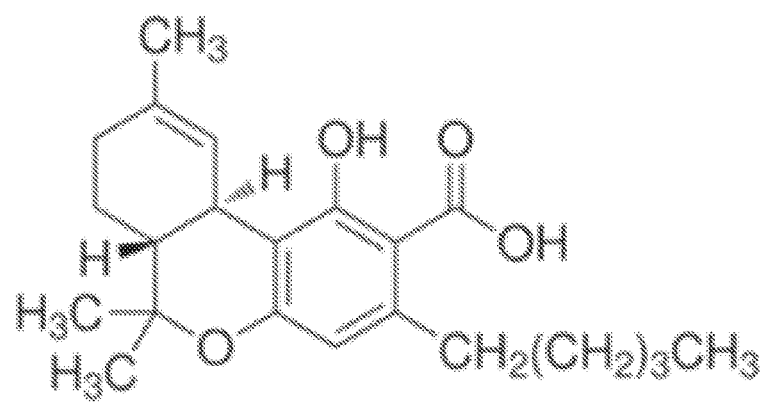
FIG. 9A is a skeletal formula representing a chemical structure of tetrahydrocannabinolic acid.

FIG. 9A is a skeletal formula representing a chemical structure of tetrahydrocannabinolic acid. In some embodiments, tetrahydrocannabinolic acid refers to (6aR,10aR)-1-hydroxy-6,6,9-trimethyl-3-pentyl-6a,7,8,10a-tetrahydro-6h-benzo[c]chromene-2-carboxylic acid.

Figure 9B:
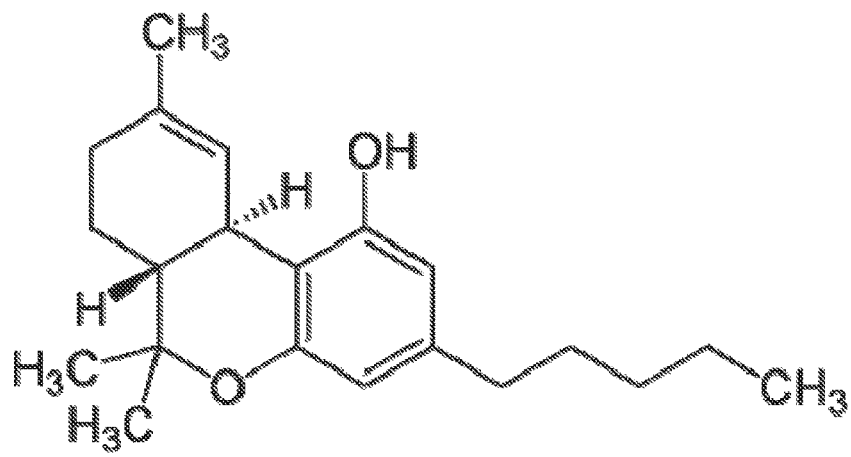
FIG. 9B is a skeletal formula representing a chemical structure of tetrahydrocannabinol.

FIG. 9B is a skeletal formula representing a chemical structure of tetrahydrocannabinol. In some embodiments, the term tetrahydrocannabinol refers to (−)-(6aR,10aR)-6,6,9-Trimethyl-3-pentyl-6a,7,8,10a-tetrahydro-6H-benzo[c]chromen-1-ol. In some embodiments, tetrahydrocannabinol is also called (−)-trans-$\Delta^9$-tetrahydrocannabinol.

Figure 9C:
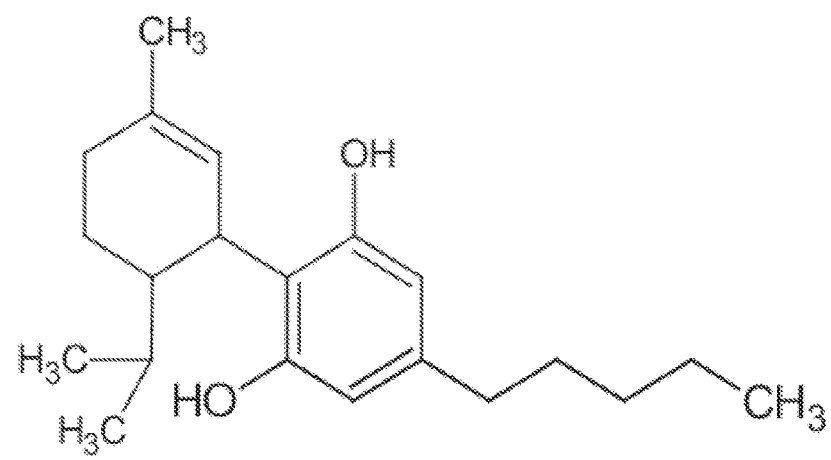
FIG. 9C is a skeletal formula representing a chemical structure of cannabidiol.

FIG. 9C is a skeletal formula representing a chemical structure of cannabidiol. In some embodiments, cannabidiol refers to 2-[(1R,6R)-6-isopropenyl-3-methylcyclohex-2-en-1-yl]-5-pentylbenzene-1,3-diol.

Although FIGS. 9A-9C illustrate particular skeletal formulas of the exemplary chemicals, a person having ordinary skill in the art would understand that a same chemical may be represented using different skeletal formulas. For example, the $CH_2(CH_2)_3CH_3$ chain shown in FIG. 9A may be represented using multiple connections of carbon atoms (e.g., $CH_2$), as represented in FIGS. 9B and 9C. Optionally, stereochemistry may be also indicated in skeletal formulas, as shown in FIGS. 9A and 9B.

As described above, in some embodiments, a beverage container (e.g., a can, a bottle, etc.) for preparing a beverage containing cannabinoids includes a hollow container (e.g., a body of the can or the bottle) with a first reservoir and a second reservoir distinct from the first reservoir. Both the first reservoir and the second reservoir are positioned within the hollow container (e.g., see FIG. 2A). The first reservoir is configured to store an aqueous beverage (e.g., still or sparkling, flavored or non-flavored, etc.). The second reservoir sealingly stores one or more polymer matrices that include cannabinoid compounds. The second reservoir prevents an exposure of the one or more polymer matrices to the aqueous beverage prior to the second reservoir being opened. The second reservoir is configured to release the one or more polymer matrices stored in the second reservoir into the aqueous beverage subsequent to the second reservoir being opened (e.g., breaking the separation layer 250 shown in FIG. 2B).

The hollow container defines an opening through which a liquid in the hollow container is allowed to egress from the hollow container (e.g., the opening 120 in FIG. 1B). In some embodiments, the one or more polymer matrices are stored in the second reservoir in a liquid form. In some embodiments, the one or more polymer matrices are stored in the second reservoir in a solid form (e.g., a pellet, a film, a tablet, powders, etc.).

The beverage container also includes a closure sealingly and operably coupled with the opening of the hollow container (e.g., the portion of the lid 110 that also corresponds to the opening 120 when the beverage container is closed). The closure is operably coupled with the second reservoir such that opening of the closure initiates opening of the second reservoir (e.g., see FIGS. 2A-2C). The closure seals the opening of the hollow container and prevents egress, from the hollow container, of the aqueous beverage or the one or more polymer matrices stored in the hollow container prior to the closure being opened (e.g., see FIG. 2A). The closure allows egress of the aqueous beverage and the one or more polymer matrices subsequent to the closure being opened (e.g., see FIG. 2C).

As discovered by the inventors, a potency of the cannabinoid compounds decreases over time subsequent to releasing the cannabinoid compounds stored in the second reservoir into the aqueous beverage.

In some embodiments, the cannabinoid compounds include one or more of: tetrahydrocannabinolic acid, tetrahydrocannabinol, and cannabidiol. In some embodiments, the cannabinoid compounds include tetrahydrocannabinolic acid. In some embodiments, the cannabinoid compounds include tetrahydrocannabinol. In some embodiments, the cannabinoid compounds include cannabidiol. However, a person having ordinary skill in the art would understand that other forms of cannabinoids, naturally occurring or modified or synthesized, can be included in the beverage container in an analogous manner.

In some embodiments, the beverage container is configured to retain the second reservoir in place prior to the closure being opened and release the second reservoir into the aqueous beverage upon the closure being opened (e.g., see FIG. 5A). For example, in some embodiments, the second reservoir is separate from the first reservoir (e.g., the second reservoir is a part that can move independently within the first reservoir). Prior to the closure being opened, the second reservoir is retained in place within the first reservoir. For example, the second reservoir is held adjacent to the closure or attached to the lid of the beverage container. This prevents the second reservoir from moving within the first reservoir. When the closure is opened, the second reservoir is released (e.g., detached), which allows the second reservoir to drop into the aqueous beverage stored within the first reservoir (e.g., see FIGS. 5B and 5C). In some embodiments, the beverage container has a pull-tab and the second reservoir is released upon pulling the pull-tab to open the beverage container (e.g., FIGS. 5A-5C). For example, in some embodiments, the secondary container is held by a latch mechanism coupled with the pull-tab, and the secondary container is released by the latch mechanism, initiated by pulling the pull-tab. In some embodiments, the beverage container has a rotatable closure, and the secondary container is held by a coupler to a lid (or a top surface) of the beverage container. In some embodiments, the coupler is configured to break in response to a rotation of the rotatable closure, thereby releasing the second reservoir into the beverage stored in the first reservoir. In another example, in some embodiments, the secondary container has a threaded hole and is held by a threaded object (e.g., a screw) coupled to the rotatable closure. Upon rotating the rotatable closure, the second reservoir is released (e.g., see FIGS. 6B and 6D).

In some embodiments, the hollow container is a can (e.g., the can 100 in FIG. 1). In some embodiments, the can is a cylindrical receptacle. In some embodiments, the can is made of metal. In some embodiments, the can is made of aluminum. In some embodiments, the can is made of plastic. In some embodiments, the can is made of glass. In some embodiments, the can includes glass. In some embodiments, the opening of the hollow container is defined by one or more grooves in a lid of the hollow container. In some embodiments, a lid of the can refers to a generally planar surface of the can. In some embodiments, the one or more grooves are formed by scoring the lid of the hollow container.

In some embodiments, the closure includes a tab (e.g., tab 130 along with a portion of the lid 110 corresponding to the lid 120 in FIG. 1B). In some embodiments, the closure is a tab. In some embodiments, the tab is a pull-tab. In some embodiments, the tab is a stay-on-tab (e.g., tab 130 in FIG. 1B). In some embodiments, the closure is rotatable. For example, in some embodiments, the closure (sometimes called a twist-and-shut) is rotated to open or close the beverage container (e.g., see FIGS. 6A and 6C). In some embodiments, the closure is a lid. In some embodiments, the can is a full-aperture can, and the closure is a lid of the full-aperture can.

In some embodiments, the can includes one or more sidewalls, a top surface, a bottom surface, and a separation layer positioned between the top surface and the bottom surface, the separation layer being positioned adjacent to the top surface. The first reservoir is defined by the separation layer, the bottom surface, and at least a portion of the one or more sidewalls (e.g., the first reservoir 210 in FIG. 2A). The second reservoir is defined by the top surface, the separation layer, and at least a portion of the one or more sidewalls (e.g., the second reservoir 220 in FIG. 2A).

In some embodiments, the separation layer defines a second opening through which the one or more polymer matrices in the second reservoir are allowed to migrate into the first reservoir (e.g., see FIGS. 3B-3E). In some embodiments, the second opening in the separation layer is aligned with the opening of the hollow container (e.g., the opening 310 in FIG. 3B).

In some embodiments, the second reservoir is adapted for opening by puncturing the separation layer (e.g., FIGS. 2A-2B). In some embodiments, the separation layer is configured for puncturing. For example, in some embodiments, the separation layer is made of a material that is easy for puncturing (e.g., a wax paper or a plastic film). In some embodiments, the separation layer has a predefined thickness that allows the separation layer to be punctured by a force substantially equal to a force used for opening the beverage container (e.g., not more than twice the force needed for opening the beverage container). As used herein, in some cases, the term puncturing refers to breaking or tearing (of the separation layer).

In some embodiments, the separation layer is made of metal. In some embodiments, the separation layer is made of a metal sheet. In some embodiments, the separation layer is made of aluminum. In some embodiments, the separation layer is made of an aluminum sheet. In some embodiments, the separation layer and the hollow container are made of a same material. In some embodiments, the separation layer and the hollow container are made of distinct materials. In some embodiments, the separation layer and the hollow container are formed integrally.

In some embodiments, the separation layer is made of plastic.

In some embodiments, the tab and a lid of the can are formed integrally.

In some embodiments, the hollow container is a bottle (e.g., the bottle 700 in FIG. 7).

In some embodiments, the closure includes a cap (also called herein, a lid or a top). In some embodiments, the closure is a cap. In some embodiments, the cap is a screw top. In some embodiments, the cap is a crown cap.

In some embodiments, the cap includes an object (e.g., the object 820 in FIG. 8A) located within the cap. In some embodiments, the object is located at least partially within the cap. In some embodiments, the object is located entirely within the cap. In some embodiments, the object is located entirely within the beverage container. In some embodiments, the object is located at least partially outside the beverage container. The cap has one or more protrusions and/or indentations, adjacent to the opening of the hollow container, on an inner surface of the cap (e.g., protrusions and/or indentations 810 in FIG. 8A). The one or more protrusions and/or indentations define a neck having a diameter smaller than a representative dimension of the object, and the neck prevents egress, from the beverage container, of the object at least partially located within the cap. The object is sealingly positioned in contact with the one or more protrusions and/or indentations, and prevents egress, from the beverage container, of the aqueous beverage or the one or more polymer matrices stored in the beverage container prior to the closure being opened. In some embodiments, the object is sealingly positioned in contact with the one or more protrusions and/or indentations by an interference fit (also known as a press fit or a friction fit). In some embodiments, a pressure difference between the pressure inside the beverage container and the pressure outside the beverage container causes the spherical object to be sealingly positioned in contact with the one or more protrusions and/or indentations and pressing the spherical object toward the one or more protrusions and/or indentations.

In some embodiments, the closure is a spherical object (e.g., the object 820 in FIG. 8A). In some embodiments, the representative dimension is a diameter of the spherical object. In some embodiments, when the closure is a cone, the representative dimension is a diameter of a bottom surface of the cone. In some embodiments, the aqueous beverage is carbonated. In such embodiments, the pressure inside the beverage container is higher than an atmospheric pressure prior to the closure being opened.

In some embodiments, the beverage container includes one or more inner sidewalls of the bottle, one or more inner sidewalls of the cap, an inner bottom surface of the bottle, and a separation layer, positioned inside the beverage container and adjacent to the one or more protrusions and/or indentations, and between the object and the bottom surface. The first reservoir is defined by the separation layer, the bottom surface, at least a portion of the one or more inner sidewalls of the bottle, and at least a portion of the one or more inner sidewalls of the cap. The second reservoir is defined at least by the object, at least a portion of the one or more protrusions and/or indentations, and the separation layer (e.g., see FIG. 8A, in which the separation layer 250 is attached to protrusions and/or indentations 810).

In some embodiments, the second reservoir is further defined by at least a portion of the one or more inner sidewalls of the cap (e.g., see FIG. 8B, in which the separation layer 250 is attached to sidewalls 830).

In some embodiments, the separation layer has a shape of a cup (e.g., the separation layer 250 in FIG. 8C). In some embodiments, a cup has one or more sidewalls and a bottom surface with an opening on top.

In some embodiments, the cap defines a through hole (e.g., the cap 840 in FIG. 8D). The cap has a first wall and a second wall on an inner surface of the cap, wherein the first wall has a first wall diameter and the second wall has a second wall diameter larger than the first wall diameter. The cap includes an object at least partially located within the cap, adjacent to the opening of the hollow container, on an inner surface of the cap. The first wall prevents egress, from the beverage container, of the object at least partially located within the cap. The object is sealingly positioned in contact with the first wall and the second wall, preventing egress, from the beverage container, of the aqueous beverage or the cannabinoid compounds stored in the beverage container prior to the closure being opened. The beverage container includes one or more inner sidewalls of the bottle and an inner bottom surface of the bottle. The first reservoir is defined by the bottom surface of the bottle, at least a portion of the one or more side walls of the bottle, and at least a portion of the cap. In some embodiments, the first reservoir is defined by the bottom surface of the bottle, at least a portion of the one or more inner sidewalls of the bottle, at least a portion of an outer layer of the cap, and at least a portion of the second wall of the cap. The second reservoir is located between at least a portion of the first wall and at least a portion of the second wall. In some embodiments, the second reservoir is defined at least by the object, at least a portion of the first wall, at least a portion of the second wall, and at least a portion of the outer layer of the cap.

In some embodiments, the second wall includes one or more protrusions and/or indentations (e.g., one or more protrusions and/or indentations 874 in FIG. 8D) for releasably positioning the object in contact with the first wall and the second wall.

Figure 10:
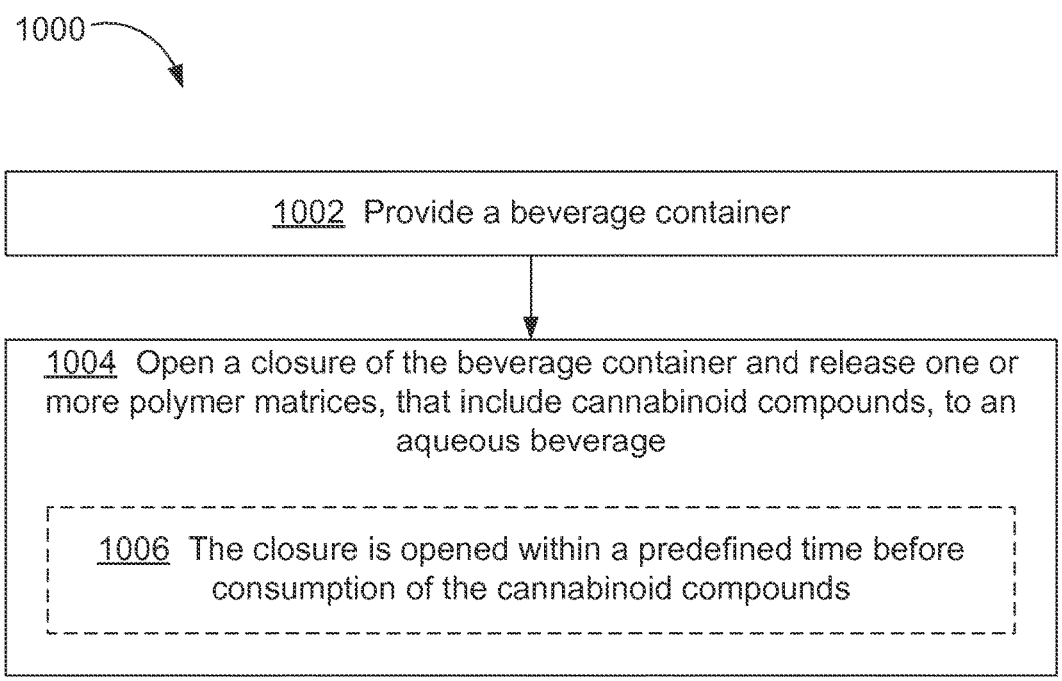
FIG. 10 is a flowchart illustrating a method for preparing a beverage containing cannabinoids in accordance with some embodiments.

FIG. 10 is a flowchart illustrating a method 1000 for preparing a beverage containing cannabinoids in accordance with some embodiments.

The method 1000 includes (1002) providing any beverage container described above (e.g., the can in FIG. 4A or the bottle in FIG. 8A).

The method also includes (1004) opening the closure of the beverage container and releasing one or more polymer matrices, that include cannabinoid compounds, to the aqueous beverage (e.g., see FIGS. 2B-2C). In some embodiments, the method includes mixing the one or more polymer matrices and the aqueous beverage inside the beverage container. As a result, a cannabinoid beverage is formed (e.g., the cannabinoid beverage 260 in FIG. 2C).

In some embodiments, the closure is opened (1006) within a predefined time before consumption of the cannabinoid compounds. In some embodiments, the predefined time is one of: one day, twelve hours, six hours, three hours, two hours, one hour, thirty minutes, and fifteen minutes. Because the cannabinoid compounds are mixed with the aqueous beverage within the predefined time before the consumption (in some cases, immediately before the consumption), the degradation of a potency of the cannabinoid compounds in the aqueous beverage is reduced. This significantly increases a shelf-life in providing a cannabinoid beverage. In some cases, by separately storing the one or more polymer matrices and an aqueous beverage, it is expected that the shelf-life can exceed two years, which is significantly more than a current shelf-life of cannabinoid beverages.

FIG. 11 is a flowchart illustrating a method 1100 for preparing a beverage containing cannabinoids in accordance with some embodiments.

The method 1100 includes (1102) providing a beverage container separately storing an aqueous beverage and one or more polymer matrices that include cannabinoid compounds without exposing the one or more polymer matrices to the aqueous beverage (e.g., see FIG. 2A). The beverage container includes a closure that prevents egress, from the beverage container, of the aqueous beverage or the one or more polymer matrices stored in the beverage container.

In some embodiments, the aqueous beverage is stored (1104) in a first reservoir in the beverage container (e.g., the aqueous beverage 230 in the first reservoir 210, as shown in FIG. 2A). The first reservoir is configured to allow egress, from the first reservoir, of the aqueous beverage in the first reservoir subsequent to the closure being opened. The one or more polymer matrices are stored in a second reservoir, distinct from the first reservoir, in the beverage container (e.g., the cannabinoid compounds 240 in the second reservoir 220 as shown in FIG. 2A). The second reservoir is configured to allow release of the one or more polymer matrices, from the second reservoir, into the aqueous beverage subsequent to the closure being opened.

In some embodiments, the cannabinoid compounds include (1106) one or more of: tetrahydrocannabinolic acid, tetrahydrocannabinol, and cannabidiol. In some embodiments, the cannabinoid compounds include tetrahydrocannabinol (e.g., see FIG. 9B). In some embodiments, the cannabinoid compounds include cannabidiol (e.g., see FIG. 9C). In some embodiments, the cannabinoid compounds include tetrahydrocannabinolic acid (e.g., see FIG. 9A).

The method 1100 includes (1108) releasing the one or more polymer matrices to the aqueous beverage by opening the closure (e.g., see FIGS. 2B and 2C). In some embodiments, the method includes mixing the one or more polymer matrices and the aqueous beverage inside the beverage container.

In some embodiments, the closure is opened (1110) within a predefined time before consumption of the cannabinoid compounds.

In some embodiments, the predefined time is (1112) one of: one day, twelve hours, six hours, three hours, two hours, one hour, thirty minutes, and fifteen minutes. In some embodiments, the predefined time is one day. In some embodiments, the predefined time is twelve hours. In some embodiments, the predefined time is three hours. In some embodiments, the predefined time is two hours. In some embodiments, the predefined time is one hour. In some embodiments, the predefined time is thirty minutes. In some embodiments, the predefined time is fifteen minutes.

In some embodiments, a potency of the cannabinoid compounds decreases (1114) over time subsequent to releasing the cannabinoid compounds into the aqueous beverage.

Although the beverage containers above are described as containing cannabinoid compounds, in some embodiments, the beverage containers do not include the cannabinoid compounds (e.g., before providing the cannabinoid compounds into the beverage containers). Thus, in some embodiments, a beverage container includes a hollow container with a first reservoir and a second reservoir distinct from the first reservoir, both the first reservoir and the second reservoir positioned within the hollow container, the first reservoir configured to store an aqueous beverage, the second reservoir configured for sealingly storing cannabinoid compounds, the second reservoir preventing an exposure of the cannabinoid compounds to the aqueous beverage prior to the second reservoir being opened, the second reservoir being configured to release the cannabinoid compounds stored in the second reservoir into the aqueous beverage subsequent to the second reservoir being opened, the hollow container defining an opening through which a liquid in the hollow container is allowed to egress from the hollow container. The beverage container also includes a closure sealingly and operably coupled with the opening of the hollow container, the closure operably coupled with the second reservoir such that opening of the closure initiates opening of the second reservoir, the closure sealing the opening of the hollow container and preventing egress, from the hollow container, of the aqueous beverage or the cannabinoid compounds stored in the hollow container prior to the closure being opened, the closure allowing egress of the aqueous beverage and the cannabinoid compounds subsequent to the closure being opened.

In some embodiments, one or more polymer matrices include one or more of: polyethylene oxide, polyvinyl alcohol, hydroxypropyl methyl cellulose, polyoxazoline, polyethylene glycol, polyvinyl pyrrolidone, polyvinyl-pyrrolidone polyvinylacetate copolymer, hydroxypropyl cellulose, polyurethane, poloxamer (e.g., polyoxyethylene-polyoxypropylene block copolymer), polyvinyl caprolactam-polyvinyl acetate-polyethylene glycol graft copolymer, pectin, chitosan, polycarbophil, alginate, hyaluronan, agar, dextran, pullulan, polyglycolide, poly(DL-lactide-co-glycolide), or any combination thereof.

In some embodiments, a polymer matrix of the one or more polymer matrices includes at least 20 wt. % of polyoxazoline. In some embodiments, the polymer matrix of the one or more polymer matrices includes at least 50 wt. % of polyoxazoline. In some embodiments, the polyoxazoline has a molar mass of at least 40,000 g/mol. In some embodiments, the polyoxazoline has a molar mass of at least 80,000 g/mol. In some embodiments, the polyoxazoline has a molar mass of at least 150,000 g/mol. In some embodiments, the polyoxazoline has a molar mass of at least 200,000 g/mol. In some embodiments, the polymer matrix of the one or more polymer matrices includes at least 0.001% by weight of cannabinoid compounds. In some embodiments, the polymer matrix of the one or more polymer matrices includes at least 0.1% by weight of cannabinoid compounds. In some embodiments, the polymer matrix of the one or more polymer matrices includes 0.5-30% by weight of cannabinoid compounds. In some embodiments, the polymer matrix of the one or more polymer matrices includes at least 70% by weight of cannabinoid compounds. In some embodiments, the polyoxazoline is a homopolymer of 2-alkyl-oxazoline. In some embodiments, the 2-alkyl-oxazoline is selected from 2-methyl-oxazoline, 2-ethyl-oxazoline, 2-propyl-oxazoline, 2-butyl-oxazoline and any combination thereof.

While particular embodiments are described above, it will be understood that the scope of claims are not limited to these particular embodiments. On the contrary, the claims include alternatives, modifications and equivalent embodiments that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description herein is for the purpose of describing particular embodiments only and is not intended to limit the scope of claims. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

It will also be understood that, although the terms first, second, etc. may be used herein to describe various elements, these elements should not be limited by these terms. These terms are only used to distinguish one element from another. For example, a first reservoir could be termed a second reservoir, and, similarly, a second reservoir could be termed a first reservoir, without departing from the scope of the claims. The first reservoir and the second reservoir are both reservoirs, but they are not the same reservoir.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen and described in order to best explain the principles described herein and their practical applications, to thereby enable others skilled in the art to best utilize various embodiments with various modifications as are suited to the particular use contemplated.

What is claimed is:

1. A beverage container for preparing a beverage containing cannabinoids, comprising:
    a hollow container with a first reservoir and a second reservoir distinct from the first reservoir, both the first reservoir and the second reservoir positioned within the hollow container, the first reservoir configured to store an aqueous beverage, the second reservoir sealingly storing one or more polymer matrices that include cannabinoid compounds, the second reservoir preventing an exposure of the one or more polymer matrices to the aqueous beverage prior to the second reservoir being opened, the second reservoir being configured to release the one or more polymer matrices stored in the second reservoir into the aqueous beverage subsequent to the second reservoir being opened, the hollow container defining an opening through which a liquid in the hollow container is allowed to egress from the hollow container; and a closure sealingly and openably coupled with the opening of the hollow container, the closure operably coupled with the second reservoir such that opening of the closure initiates opening of the second reservoir, the closure sealing the opening of the hollow container and preventing egress, from the hollow container, of the aqueous beverage or the one or more polymer matrices stored in the hollow container prior to the closure being opened, the closure allowing egress of the aqueous beverage and the one or more polymer matrices subsequent to the closure being opened, wherein the hollow container is a bottle, wherein:

the closure includes a cap;

the cap includes an object at least partially located within the cap, the cap having one or more protrusions and/or indentations, adjacent to the opening of the hollow container, on an inner surface of the cap, the one or more protrusions and/or indentations defining a neck having a diameter smaller than a representative dimension of the object, the neck preventing egress, from the beverage container, of the object at least partially located within in the cap, the object being sealingly positioned in contact with the one or more protrusions and/or indentations, preventing egress, from the beverage container, of the aqueous beverage or the cannabinoid compounds stored in the beverage container prior to the closure being opened;

the beverage container includes one or more inner sidewalls of the bottle, one or more inner sidewalls of the cap, an inner bottom surface of the bottle, and a separation layer, positioned inside the beverage container and adjacent to the one or more protrusions and/or indentations, and between the object and the bottom surface;

the first reservoir is defined by the separation layer, the bottom surface, at least a portion of the one or more inner sidewalls of the bottle, and at least a portion of the one or more inner sidewalls of the cap; and the second reservoir is defined at least by the object, at least a portion of the one or more protrusions and/or indentations, and the separation layer.

2. The beverage container of claim 1, wherein the separation layer has a shape of a cup.

3. The beverage container of claim 1, wherein the one or more polymer matrices include one or more of: polyethylene oxide, polyvinyl alcohol, hydroxypropyl methyl cellulose, polyoxazoline, polyethylene glycol, polyvinyl pyrrolidone, polyvinyl-pyrrolidone polyvynylacetate copolymer, hydroxypropyl cellulose, polyurethane, poloxamer, polyvinyl caprolactam-polyvinyl acetate-polyethylene glycol graft copolymer, pectin, chitosan, polycarbophil, alginate, hyaluronan, agar, dextran, pullulan, polyglycolide, and poly(DL-lactide-co-glycolide).

4. A method for preparing a beverage containing cannabinoids, comprising:

providing the beverage container of claim 1; and opening the closure of the beverage container and releasing the one or more polymer matrices to the aqueous beverage.

5. The method of claim 4, wherein the closure is opened within a predefined time before consumption of the cannabinoid compounds.

6. A beverage container for preparing a beverage containing cannabinoids, comprising:

a hollow container with a first reservoir and a second reservoir distinct from the first reservoir, both the first reservoir and the second reservoir positioned within the hollow container, the first reservoir configured to store an aqueous beverage, the second reservoir sealingly storing one or more polymer matrices that include cannabinoid compounds, the second reservoir preventing an exposure of the one or more polymer matrices to the aqueous beverage prior to the second reservoir being opened, the second reservoir being configured to release the one or more polymer matrices stored in the second reservoir into the aqueous beverage subsequent to the second reservoir being opened, the hollow container defining an opening through which a liquid in the hollow container is allowed to egress from the hollow container; and a closure sealingly and openably coupled with the opening of the hollow container, the closure operably coupled with the second reservoir such that opening of the closure initiates opening of the second reservoir, the closure sealing the opening of the hollow container and preventing egress, from the hollow container, of the aqueous beverage or the one or more polymer matrices stored in the hollow container prior to the closure being opened, the closure allowing egress of the aqueous beverage and the one or more polymer matrices subsequent to the closure being opened, wherein the hollow container is a bottle, wherein:

the closure includes a cap;

the cap defines a through hole;

the cap has a first wall and a second wall on an inner surface of the cap, wherein the first wall has a first wall diameter and the second wall has a second wall diameter larger than the first wall diameter;

the cap includes an object at least partially located within the cap, adjacent to the opening of the hollow container, on an inner surface of the cap, the first wall preventing egress, from the beverage container, of the object at least partially located within the cap, the object being sealingly positioned in contact with the first wall and the second wall, preventing egress, from the beverage container, of the aqueous beverage or the cannabinoid compounds stored in the beverage container prior to the closure being opened;

the beverage container includes one or more inner sidewalls of the bottle and an inner bottom surface of the bottle;

the first reservoir is defined by the bottom surface of the bottle, at least a portion of the one or more inner sidewalls of the bottle, and at least a portion of the cap; and the second reservoir is located between at least a portion of the first wall and at least a portion of the second wall.

7. The beverage container of claim 6, wherein the second wall includes one or more protrusions and/or indentations for releasably positioning the object in contact with the first wall and the second wall.

8. The beverage container of claim 6, wherein the one or more polymer matrices include one or more of: polyethylene oxide, polyvinyl alcohol, hydroxypropyl methyl cellulose polyoxazoline, polyethylene glycol, polyvinyl pyrrolidone, polyvinyl-pyrrolidone polyvynylacetate copolymer, hydroxypropyl cellulose, polyurethane, poloxamer, polyvinyl caprolactam-polyvinyl acetate-polyethylene glycol graft copolymer, pectin, chitosan, polycarbophil, alginate, hyaluronan, agar, dextran, pullulan, polyglycolide, and poly(DL-lactide-co-glycolide).

9. A method for preparing a beverage containing cannabinoids, comprising:
   providing the beverage container of claim 6; and
   opening the closure of the beverage container and releasing the one or more polymer matrices to the aqueous beverage.

10. The method of claim 9, wherein the closure is opened within a predefined time before consumption of the cannabinoid compounds.

* * * * *